United States Patent
Alsberg et al.

(10) Patent No.: US 12,151,047 B2
(45) Date of Patent: Nov. 26, 2024

(54) HYDROGEL FOR TISSUE ENGINEERING AND BIOPRINTING

(71) Applicant: CASE WESTERN RESERVE UNIVERSITY, Cleveland, OH (US)

(72) Inventors: Eben Alsberg, Cleveland, OH (US); Oju Jeon, Cleveland, OH (US); Jung-Youn Shin, Cleveland, OH (US); Robyn Marks, Cleveland, OH (US); Mitchell Hopkins, Cleveland, OH (US); Hongyun Park, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 598 days.

(21) Appl. No.: 16/641,056

(22) PCT Filed: Jul. 25, 2018

(86) PCT No.: PCT/US2018/043643
§ 371 (c)(1),
(2) Date: Feb. 21, 2020

(87) PCT Pub. No.: WO2019/040224
PCT Pub. Date: Feb. 28, 2019

(65) Prior Publication Data
US 2021/0046220 A1  Feb. 18, 2021

Related U.S. Application Data

(60) Provisional application No. 62/548,243, filed on Aug. 21, 2017.

(51) Int. Cl.
| | |
|---|---|
| *A61L 27/44* | (2006.01) |
| *A61L 27/20* | (2006.01) |
| *A61L 27/26* | (2006.01) |
| *A61L 27/36* | (2006.01) |
| *A61L 27/38* | (2006.01) |
| *A61L 27/52* | (2006.01) |
| *A61L 27/54* | (2006.01) |
| *A61L 27/58* | (2006.01) |
| *C08B 37/00* | (2006.01) |
| *C08G 65/00* | (2006.01) |
| *C08H 1/06* | (2006.01) |
| *C08L 5/04* | (2006.01) |
| *C08L 89/06* | (2006.01) |

(52) U.S. Cl.
CPC ............. *A61L 27/44* (2013.01); *A61L 27/20* (2013.01); *A61L 27/26* (2013.01); *A61L 27/3608* (2013.01); *A61L 27/3834* (2013.01); *A61L 27/52* (2013.01); *A61L 27/54* (2013.01); *A61L 27/58* (2013.01); *C08B 37/0084* (2013.01); *C08G 65/002* (2013.01); *C08H 1/06* (2013.01); *C08L 5/04* (2013.01); *C08L 89/06* (2013.01); *A61L 2300/236* (2013.01); *A61L 2300/252* (2013.01); *A61L 2300/412* (2013.01); *A61L 2300/414* (2013.01); *A61L 2400/16* (2013.01); *A61L 2430/40* (2013.01); *C08L 2205/04* (2013.01); *C08L 2312/00* (2013.01)

(58) Field of Classification Search
CPC ...................... A61L 27/20–60; C08B 37/0084
See application file for complete search history.

(56) References Cited

U.S. PATENT DOCUMENTS

| | | | |
|---|---|---|---|
| 8,388,948 | B2 | 3/2013 | Basu et al. |
| 9,370,606 | B2 | 6/2016 | Nakamura et al. |
| 9,642,914 | B2 | 5/2017 | Alsberg et al. |
| 2008/0226692 | A1 | 9/2008 | Sato et al. |
| 2016/0022862 | A1 | 1/2016 | Alsberg et al. |
| 2016/0279868 | A1 | 9/2016 | Burdick et al. |
| 2017/0189581 | A1 | 7/2017 | Desai et al. |
| 2017/0327813 | A1 | 11/2017 | Cattolico et al. |

FOREIGN PATENT DOCUMENTS

WO      90/10454 A1      9/1990

OTHER PUBLICATIONS

Guermani, E. et al."Engineering complex tissue-like microgel arrays . . . " Sci. Rep., vol. 6, pp. 1-8. (Year: 2016).*
Neves, L. et al."Injectable hyaluronic acid hydrogels . . . " Regen. Eng. Transl. Med., vol. 3, pp. 53-69. (Year: 2017).*
Babo, P. et al "Platelet lysate membranes . . . " J. Tiss. Eng. Regen. Med., vol. 34, No. 1, pp. 33-44. (Year: 2014).*
Becker, T. et al "Calcium alginate gel . . . " J. Biomed. Mater. Res., vol. 4, pp. 76-86. (Year: 2011).*
Andersen, T. et al "3D cell culture in alginate hydrogels" Microarrays, vol. 4, pp. 133-161. (Year: 2015).*
Wang, M. et al "Novel crosslinked alginate/hyaluronic acid hydrogels . . . " Front. Mater. Sci., vol. 7, No. 3, pp. 269-284. (Year: 2013).*
Rouillard, A. et al "Methods for photocrosslinking alginate hydrogels . . . " Tiss. Eng.: Part C, vol. 17, No. 2, pp. 173-179. (Year: 2011).*
Tasoglu, S. et al "Bioprinting for stem cell research" Trends Biotechnol., vol. 31, No. 1, pp. 10-19. (Year: 2013).*
Taylor, D. et al "Self-healing hydrogels" Adv. Mater., vol. 28, pp. 9060-9093. (Year: 2016).*
Hinton, T. et al "Three-dimensional printing of complex biological structures . . . " Sci. Adv., vol. 1, No. 9, pp. 1-10. (Year: 2015).*
Skardal et al., "Photocrosslinkable Hyaluronan-Gelatin Hydrogels for Two-Step Bioprinting", Tissue Engineering: Part A, vol. 16 No. 8 (May 6, 2010): pp. 2675-2685.

(Continued)

*Primary Examiner* — Leigh C Maier
(74) *Attorney, Agent, or Firm* — Tarolli, Sundheim, Covell & Tummino LLP

(57) ABSTRACT

A composition includes a hydrogel that includes a plurality biodegradable natural polymer macromers crosslinked with a first agent and optionally a plurality of cells dispersed in the crosslinked macromers, the microgels are capable of being crosslinked with a second agent that is different than the first crosslinking agent.

14 Claims, 23 Drawing Sheets

(56) References Cited

OTHER PUBLICATIONS

Ouyang et al., "3D Printing of Shear-Thinning Hyaluronic Acid Hydrogels with Secondary Cross-Linking" ACS Biomaterials Science & Engineering, vol. 2 Issue 10 (May 2016): pp. 1743-1751.
Jeon et al., "The effect of oxidation on the degradation of photocrosslinkable alginate hydrogels", Biomaterials, vol. 33 Issue 13 (May 2012): pp. 3503-3514.
Jenkins et al., "Glossary of Basic Terms in Polymer Science (IUPAC Recommendations 1996)", Pure and Applied Chemistry, vol. 68 Issue 12 (1996): pp. 2287-2311.
Pereira et al., "A single-component hydrogel bioink for bioprinting of bioengineered 3D constructs for dermal tissue engineering", Materials Horizons (Aug. 17, 2018): pp. 1-12.
Applicant: Case Western Reserve University; PCT International Application No. PCT/US19/26678; International Filing Date: Apr. 9, 2019; PCT International Search Report and Written Opinion; Authorized Officer: Lee W. Young; Date of Completion: Jun. 11, 2019; 11 pgs.
First Named Inventor: Eben Alsberg; U.S. Appl. No. 16/107,756, filed Aug. 21, 2018; NonFinal Office Action; dated Aug. 26, 2020; 16 pgs.
First Named Inventor: Eben Alsberg; U.S. Appl. No. 16/107,774, filed Aug. 21, 2018; NonFinal Office Action; dated Sep. 17, 2020; 16 pgs.
First Named Inventor: Eben Alsberg; U.S. Appl. No. 16/726,375, filed Dec. 24, 2019; NonFinal Office Action; dated Oct. 5, 2020.
Applicant: Case Western Reserve University, et al.; European Patent Application No. 17879074.7; Filing Date: Dec. 11, 2017; Communication pursuant to Article 94(3) EPC; Date: Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.
Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Rachelle W. Johnson, et al., "Glycoprotein130 (Gp130)/interleukin-6 (IL-6) signalling in osteoclasts promotes bone formation in periosteal and trabecular bone", Bone, vol. 81, Aug. 7, 2015, pp. 343-351.
Rozen, et al., "Fracture repair: Modulation of fracture-callus and mechanical properties by sequential application of IL-6 following PTH 1-34 or PTH 28-48, IL-6 following PTH 1-34 or PTH 28-48", Bone, Pergamon Press., Oxford, GB, vol. 41, No. 3, Aug. 8, 2007, pp. 437-445.
Xin Zhou, et al., "Chondrocytes Transdifferentiate into Osteoblasts in Endochondral Bone during Development, Postnatal Growth and Fracture Healing in Mice", Plos Genetics, vol. 10, No. 12, Dec. 4, 2014.
First Named Inventor: Eben Alsberg; U.S. Appl. No. 16/107,708, filed Aug. 21, 2018; NonFinal Office Action; dated Mar. 3, 2022; 17 pgs.
Kadri, R., et al. "Preparation and characterization of nanofunctionalized alginate/methacrylated gelatin hybrid hydrogels." RSC advances 6.33 (2016): 27879-27884.
First Named Inventor: Eben Alsberg; U.S. Appl. No. 16/044,182, filed Jul. 24, 2018; Non-Final Office Action, dated Jun. 24, 2022; 18 pgs.
First Named Inventor: Eben Alsberg; U.S. Appl. No. 16/153,138, filed Oct. 5, 2018; NonFinal Office Action; dated Aug. 12, 2022; 17 pgs.
First Named Inventor: Eben Alsberg; U.S. Appl. No. 12/191,034, filed Aug. 13, 2008; NonFinal Office Action; dated Oct. 4, 2022; 28 pgs.
First Named Inventor: Eben Alsberg; U.S. Appl. No. 16/107,756, filed Aug. 21, 2018; NonFinal Office Action; dated Nov. 17, 2022; 33 pgs.
Gomez, et al. (Carbohydrate Polymers 67 (2007) 296-304) (Year: 2007).
First Named Inventor: Eben Alsberg; U.S. Appl. No. 17/544,544, filed Dec. 7, 2021; NonFinal Office Action; dated Dec. 8, 2022; 6 pgs.
European Application No. 18848203.8, Office Action dated Mar. 5, 2024.
Alexandra L. Rutz et al: "A Multimaterial Bioink Method for 3D Printing Tunable, Cell-Compatible Hydrogels", Advanced Materials, vol. 27, No. 9, Mar. 1, 2015 (Mar. 1, 2015), pp. 1607-1614, XP055447404, ISSN: 0935-9648, DOI: 10.1002/adma.201405076.

* cited by examiner

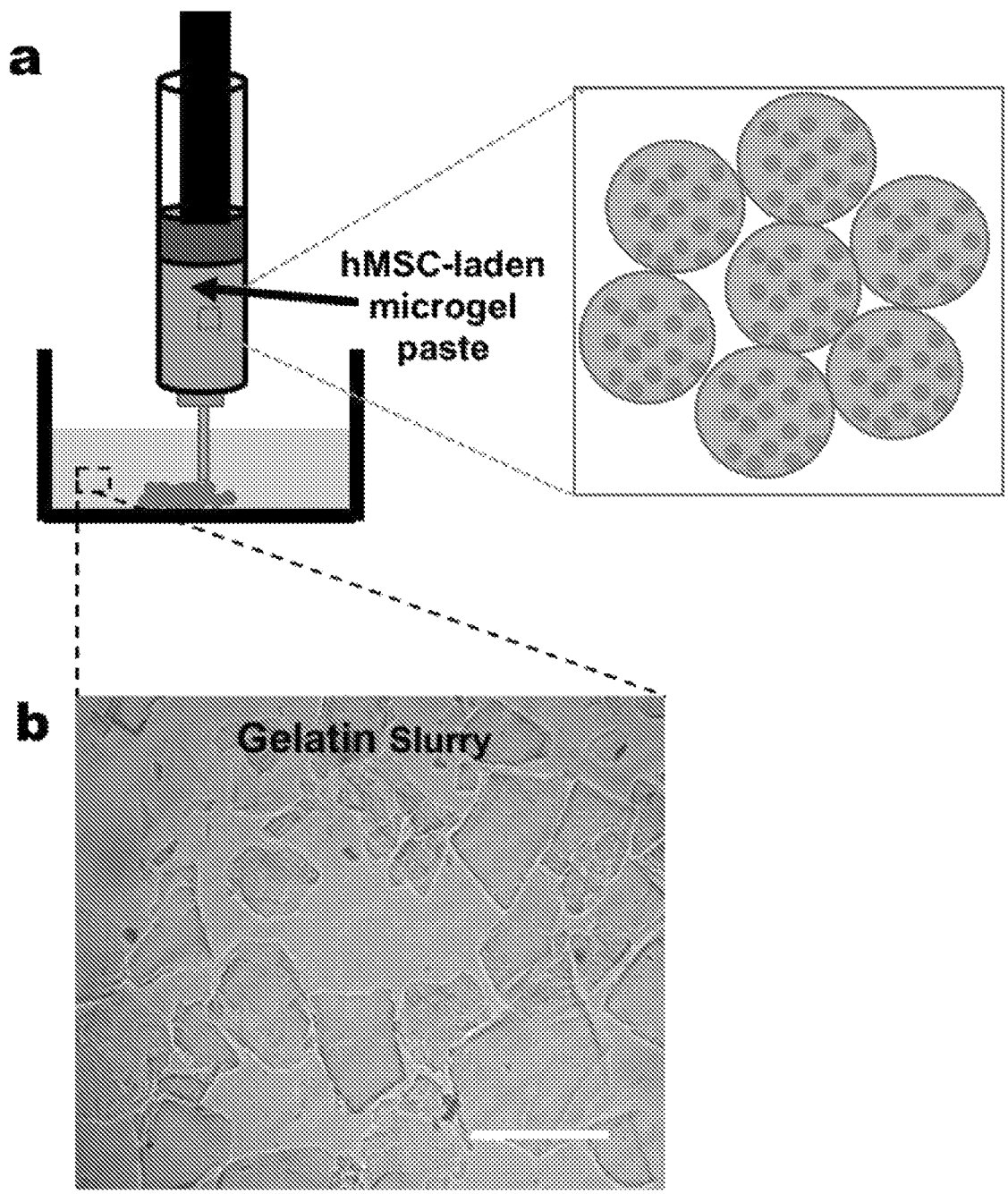
Fig. 9A-B

HYDROGEL FOR TISSUE ENGINEERING AND BIOPRINTING

RELATED APPLICATION

This application claims priority from U.S. Provisional Application No. 62/548,243, filed Aug. 21, 2017, the subject matter of which is incorporated herein by reference in its entirety.

GOVERNMENT FUNDING

This invention was made with government support under AR069564, AR066193, AR007505, and CA108512 awarded by The National Institutes of Health. The government has certain rights to the invention.

BACKGROUND

Living tissues are ensembles of modular building blocks that organize into hierarchical structures across multiple length scales from microns to meters. During the course of their development, these modules of cells and extracellular components arrange in well-defined three-dimensional (3D) microarchitectures to establish proper coordination of cell-cell and cell-extracellular matrix (ECM) interactions and generate tissue-specific function. Therefore, in context of tissue engineering, recreating the spatial organization of these modules may be necessary to build a functional tissue construct that can be used therapeutically. Conventional tissue engineering methods employ a "top-down" approach in which cells are seeded on or within a biodegradable scaffold and exposed to cues such as biochemical signals and mechanical stimulation to guide the formation of appropriate tissue organization and architecture. However, the top-down approach still faces challenges such as precisely positioning cells of multiple types, achieving tissue-specific geometries and cell densities, and incorporating vasculature throughout the three-dimensional space of the tissue constructs. To address these issues, "bottom-up" strategies are emerging as alternative means for functional tissue engineering. Distinct from the top-down approach, the bottom-up method involves starting with simplified building blocks composed of cells, materials and/or bioactive factors, and assembling them into larger, complex tissues that have organization and architecture necessary for functionality. It is possible to engineer the individual blocks in various shapes and sizes with desired types of cells or combinations of cells and materials, and then assemble them manually into an ensemble during the scale-up process. This modularity allows enhanced control over the relative spatial arrangement of cells, ECM and/or bioactive factors during the tissue construction, making it possible to engineer sophisticated architectures that mimic the native tissues.

SUMMARY

Embodiments described herein relate to compositions, devices, and methods for use in regenerative medicine, cell-based technologies, tissue engineering, and bioprinting applications, and particularly relate to compositions and formulations of hydrogels that can be used in regenerative medicine, cell-based technologies, tissue engineering, and bioprinting applications. For example, compositions containing hydrogels described herein can be used as building blocks for tissue engineering, e.g., by 3D printing, as well as for functional implantable objects for cell therapy applications. The hydrogel can optionally include a plurality of cells dispersed therein and maintain the cells in a state of high viability and functionality following cryopreservation and printing, be cytocompatible, and, upon degradation, produce substantially non-toxic products.

Advantageously, the viscosity of the hydrogel can decrease with increasing shear and/or strain on the hydrogel and increase or recover with decreased shear and/or strain. The increased shear and/or strain can be associated with extruding or printing the hydrogel, and the viscosity of the hydrogel can recover after extruding or printing the hydrogel to provide the hydrogel with a defined shape, allowing the hydrogel and hence the composition to be utilized as a bioink, which can be printed through a needle or nozzle. For example, the hydrogel can have a storage modulus (G') higher than the loss modulus (G") with decreased shear and/or strain on the hydrogel and a loss modulus (G") higher than a storage modulus (G') with increased shear and/or strain on the hydrogel.

In some embodiments, the hydrogel includes a plurality biodegradable natural polymer macromers crosslinked with a first agent and, optionally, a plurality of cells dispersed in the crosslinked macromers. The crosslinked hydrogel can be extrudable or printable into a defined shape. The crosslinked hydrogel can be optionally crosslinked with a second agent that is different than the first crosslinking agent. The hydrogel crosslinked with the second agent can form a form a flow-resistant and/or free-standing structure, such as a tissue construct, with a defined shape.

In other embodiments, the crosslinked hydrogel can be in the form of a plurality of microgels wherein each microgel includes a plurality biodegradable natural polymer macromers crosslinked with a first agent and a plurality of cells dispersed in the crosslinked macromers. The microgels can be extrudable or printable into a defined shape and then be further crosslinked to form a flow-resistant and/or free-standing structure with a defined shape.

In some embodiments, the biodegradable natural polymer macromers can include a plurality of acrylated and/or methacrylated natural polymer macromers. The acrylated and/or methacrylated, natural polymer macromers can be polysaccharides, which are optionally oxidized so that up to about 50% of the saccharide units therein are converted to aldehyde saccharide units. For example, the natural polymer macromers can include oxidized, acrylated and/or methacrylated alginates. In some embodiments, the natural polymer macromers can be ionically crosslinkable with the first agent and photocrosslinkable with the second agent.

In other embodiments, the composition can further include a cryopreservation and/or biopreservation agent. The composition including the cryopreservation and/or biopreservative agent can be cryopreserved and the cells can have a substantially equivalent viability and functionality upon thawing compared to similar cells not cryopreserved. The cryopreservation and/or biopreservation agent can be provided in the composition at an amount effective to maintain a cell viability of at least about 50%, at least about 60%, at least about 70%, at least about 80%, or at least about 90% during and after cryopreservation. For example, the composition can include an amount of cryopreservation agent, such as Dimethyl sulfoxide (DMSO), effective to retain the viability of the cells after being stored for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 months at −10 to −80° C., such as −20° C.

The cells of the compositions described herein can be any cells including, for example, undifferentiated stem cells or progenitor cells with a cell lineage potential that corresponds to the desired tissue being engineered and/or differentiated cells. The cells can be unipotent, oligopotent, multipotent, or pluripotent. In some embodiments, the cells are adult stem cells. The cells can be allogeneic or autologous. In particular embodiments, the cells include mesenchymal stem cells (MSCs). The composition can contain a single cell type, such as MSCs. However, in some embodiments, the composition contains two or more different types of cells, i.e., cells of two or more different lineages. The cells can be animal cells, such as human cells.

The composition can also include at least one bioactive agent. The bioactive agent can include, for example, at least one of BMP-2 or TGF-β.

Other embodiments described herein relate to a method of forming a construct, such as a tissue construct. The method can include providing a composition that includes a plurality biodegradable crosslinkable natural polymer macromers and, optionally, a plurality of cells dispersed in the macromers. The natural polymer macromers can be crosslinked with a first crosslinking agent to form a hydrogel. The natural polymer macromers or the crosslinked hydrogel can be printed and/or extruded into a defined shape. The singly crosslinked hydrogel optionally crosslinking can be optionally crosslinked with a second crosslinking agent after printing to further stabilize the hydrogel and form the construct. In some embodiments, the crosslinked hydrogel can include a plurality of microgels.

The hydrogel can then be printed into a defined shape. The single crosslinked macromers of the printed hydrogel can be crosslinked with a second crosslinking agent after printing to further stabilize the hydrogel and form the construct.

In some embodiments, the biodegradable natural polymer macromers can include a plurality of acrylated and/or methacrylated natural polymer macromers. The acrylated and/or methacrylated, natural polymer macromers can be polysaccharides, which are optionally oxidized so that up to about 50% of the saccharide units therein are converted to aldehyde saccharide units. For example, the natural polymer macromers can include oxidized, acrylated and/or methacrylated alginates. The natural polymer macromers can be ionically crosslinkable with the first agent and photocrosslinkable with the second agent.

In some embodiments, the bioink can printed into a stabilizing bath/gel that is effective to maintain the shape of the printed bioink. The stabilizing gel can be removed after crosslinking the bioink with the first crosslinking agent or the second crosslinking agent.

Also disclosed is a system that includes a composition or bioink described herein. The system can be configured to dispense the composition as a discrete unit. For example, each discrete unit can in some embodiments contains a controlled amount of the microgels. An example of a closed system device is a cartridge, such as a cartridge for use in a three-dimensional (3D) printer device.

BRIEF DESCRIPTION OF THE DRAWINGS

FIGS. 9A-D illustrate FRESH 3D printing of OMA microgels. (A) Schematic diagram of 3D FRESH printing. (B) Representative image of gelatin microparticles produced by blending for 90 sec. (C) 3D printed letters (CWRU) into gelatin slurry bath using Alizarin red S stained osteogenically differentiated hMSC-laden OMA microgels. (D) 3D printed and assembled cube using Toluidine blue O stained chondrogenically differentiated hMSC-laden OMA microgels.

DETAILED DESCRIPTION

Figure 1A:
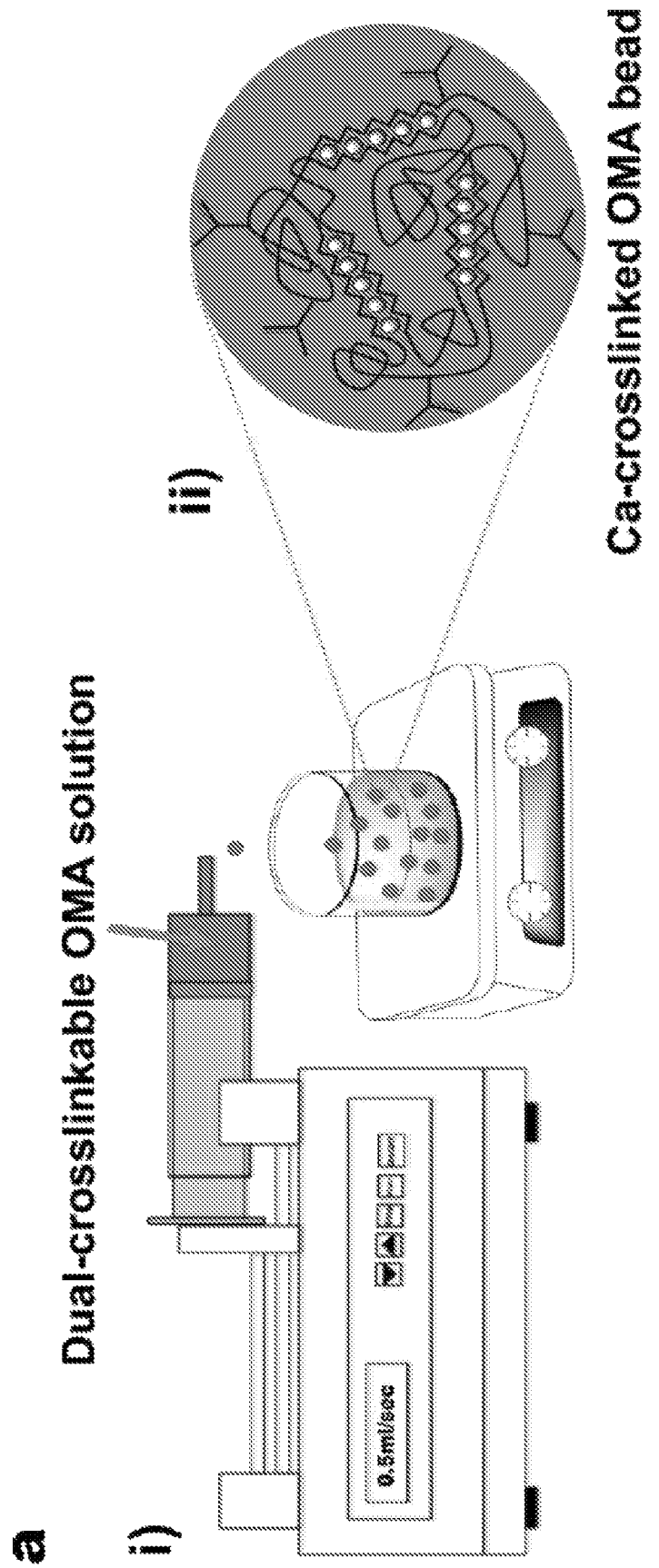
FIGS. 1A-B illustrate a fabrication and assembly of the OMA hydrogel beads. (A) Schematic depicting i) OMA bead fabrication and ii) Ca-crosslinked OMA bead. (B) Fabrication of assembled letters of manually arranged OMA beads connected by photocrosslinking. i) Ca-crosslinked OMA beads were manually arranged on a glass plate and then assembled under UV light. ii) Physically linked OMA beads in the letter C were mechanically stable. iii) Methacrylate groups were photocrosslinked under UV light between the OMA bead units to stabilize the resulting assembly. iv) Beads were manually arranged to form the letter E on a glass plate. v) OMA beads joined together via photocrosslinking could be lifted up from the glass plate. vi) Individual OMA beads detached from non-UV irradiated OMA bead samples. The scale bars indicate 10 mm.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

The term "bioactive agent" can refer to any agent capable of promoting tissue formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-βI-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

The term "biomaterial" refers to any naturally occurring, naturally derived, or synthetic material or substance which is compatible with biological systems.

The terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

The term "gel" includes gels and hydrogels.

The term "microgel" refers to hydrogels having a diameter less than about 500 μm, less than about 400 μm, or less than about 300 μm.

The term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

The term "macromer" can refer to any natural polymer or oligomer.

The term "polynucleotide" can refer to oligonucleotides, nucleotides, or to a fragment of any of these, to DNA or RNA (e.g., mRNA, rRNA, siRNA, tRNA) of genomic or synthetic origin which may be single-stranded or doublestranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

The term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

The term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprins, equines, canines, felines, ayes, etc.), which is to be the recipient of a particular treatment. Typically, the terms "patient" and "subject" are used interchangeably herein in reference to a human subject.

The term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

Embodiments described herein relate to compositions, devices, and methods for use in regenerative medicine, cell-based technologies, tissue engineering, and bioprinting applications, and particularly relate to compositions and formulations of hydrogels that can be used in regenerative medicine, cell-based technologies, tissue engineering, and bioprinting applications. For example, compositions containing hydrogels described herein can be used as building blocks for tissue engineering, e.g., by 3D printing, as well as for functional implantable objects for cell therapy applications. The hydrogel can optionally include a plurality of cells dispersed therein and maintain the cells in a state of high viability and functionality following cryopreservation and printing, be cytocompatible, and, upon degradation, produce substantially non-toxic products.

In some embodiments, the hydrogel includes a plurality biodegradable natural polymer macromers crosslinked with a first agent and, optionally, a plurality of cells dispersed in the crosslinked macromers. The crosslinked hydrogel can be extrudable or printable into a defined shape. The crosslinked hydrogel can be optionally crosslinked with a second agent that is different than the first crosslinking agent. The hydrogel crosslinked with the second agent can form a form a flow-resistant and/or free-standing structure, such as a tissue construct, with a defined shape.

In other embodiments, the crosslinked hydrogel can be in the form of a plurality of microgels wherein each microgel includes a plurality biodegradable natural polymer macromers crosslinked with a first agent and a plurality of cells dispersed in the crosslinked macromers. The microgels can be extrudable or printable into a defined shape and then be further crosslinked to form a flow-resistant and/or free-standing structure with a defined shape.

The natural polymer macromers can be any crosslinkable natural polymer or oligomer that includes a functional group (e.g., a carboxylic group) that can be further polymerized. Examples of natural polymers or oligomers are saccharides (e.g., mono-, di-, oligo-, and poly-saccharides), such as glucose, galactose, fructose, lactose and sucrose, collagen, gelatin, glycosaminoglycans, poly(hyaluronic acid), poly (sodium alginate), hyaluronan, alginate, heparin and agarose.

In some embodiments, the dual crosslinkable natural polymer macromers can include an acrylated and/or methacrylated natural polymer macromers. Acrylated and/or methacrylated natural polymer macromers can include saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose that can be readily oxidized to form free aldehyde units.

In some embodiments, the acrylated or methacrylated, natural polymer macromers are polysaccharides, which are optionally oxidized so that up to about 50% of the saccharide units therein are converted to aldehyde saccharide units. Control over the degree of oxidation of the natural polymer macromers permits regulation of the gelling time used to form the hydrogel as well as the mechanical properties, which allows for tailoring of these mechanical properties depending on the clinical application.

In other embodiments, acrylated and/or methacrylated, natural polymer macromers can include oxidized, acrylated or methacrylated, alginates, which are optionally oxidized so that up to about 50% of the saccharide units therein are converted to aldehyde saccharide units. Natural source alginates, for example, from seaweed or bacteria, are useful and can be selected to provide side chains with appropriate M (mannuronate) and G (guluronate) units for the ultimate use of the polymer. Alginate materials can be selected with high guluronate content since the guluronate units, as opposed to the mannuronate units, more readily provide sites for oxidation and crosslinking. Isolation of alginate chains from natural sources can be conducted by conventional methods. See Biomaterials: Novel Materials from Biological Sources, ed. Byrum, Alginates chapter (ed. Sutherland), p. 309-331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in Spaltro (U.S. Pat. No. 5,490,978) with other alcohols such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the natural polymer macromers (e.g., alginate material) can be performed using a periodate oxidation agent, such as sodium periodate, to provide at least some of the saccharide units of the natural polymer macromer with aldehyde groups. The degree of oxidation is controllable by the mole equivalent of oxidation agent, e.g., periodate, to saccharide unit. For example, using sodium periodate in an equivalent % of from 2% to 100%, preferably 1% to 50%, a resulting degree of oxidation, i.e., % if saccharide units converted to aldehyde saccharide units, from about 2% to 50% can be obtained. The aldehyde groups provide functional sites for crosslinking and for bonding tissue, cells, prosthetics, grafts, and other material that is desired to be adhered. Further, oxidation of the natural polymer macromer facilitates their degradation in vivo, even if they are not lowered in molecular weight. Thus, high molecular weight alginates, e.g., of up to 300,000 daltons, may be degradable in vivo, when sufficiently oxidized, i.e., preferably at least 5% of the saccharide units are oxidized.

In some embodiments, the natural polymer macromer (e.g., alginate) can be acrylated or methacrylated by reacting an acryl group or methacryl with a natural polymer or oligomer to form the oxidized, acrylated or methacrylated natural polymer macromer (e.g., alginate). For example, oxidized alginate can be dissolved in a solution chemically functionalized with N-hydroxysuccinimide and 1-ethyl-3-(3-dimethylaminopropyl)-carbodiimide hydrochloride to activate the carboxylic acids of alginate and then reacted with 2-amionethylmethacrylate to provide a plurality of methacrylate groups on the alginate.

The degree of acrylation or methacrylation can be controlled to control the degree of subsequent crosslinking of the acrylate and methacrylates as well as the mechanical properties, and biodegradation rate of the composition. The degree of acrylation or methacrylation can be about 1% to about 50%, although this ratio can vary more or less depending on the end use of the composition.

The cells dispersed in the hydrogel of the crosslinked natural polymer macromers can include any cells, such as, differentiated cells, undifferentiated cells, stem cells and/or progenitor cells with a cell lineage potential that corresponds to the desired tissue being engineered. The cells can be unipotent, oligopotent, multipotent, or pluripotent. In some embodiments, the cells are adult stem cells. The cells can be allogeneic or autologous. In particular embodiments, the cells include mesenchymal stem cells (MSCs). The composition can contain a single cell type, such as MSCs. However, in some embodiments, the composition contains two or more different types of cells, i.e., cells of two or more different lineages. The cells can be animal cells, such as human cells.

The cells can be dispersed in a solution of the natural polymer macromers. The solution of natural polymer macromers and cells can then be crosslinked with a first agent to form the hydrogel and/or plurality of microgels. Examples of crosslinking agents may include divalent cations, genipin, glutaraldehyde, tri-polyphosphate (TPP), hydroxyapitite (HA), and any other crosslinking agent known to those skilled in the art, which can be used, for example, as a bioink for generating 3D tissue constructs.

In some embodiments, the solution of natural polymer macromers and cells can be ionically crosslinked and/or chemically crosslinked with a first agent to form hydrogel. The ionically crosslinked hydrogel can be in the form of a plurality of microgels that includes the cells. By way of example, cells suspended in the solution of natural polymer macromers can be dispensed as microdroplets into an aqueous solution of $CaCl_2$ and ionically crosslinked to form the plurality of microgels. The extent of crosslinking can be controlled by the concentration of $CaCl_2$. The higher concentration can correspond to a higher extent of crosslinking. The extent of crosslinking alters the mechanical properties of the microgel and can be controlled as desired for the particular application. In general, a higher degree of crosslinking results in a stiffer gel.

The microgels can have a diameter less than about 500 μm, less than about 400 μm, or less than about 300 μm and include, for example, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 150,000, or 200,000 cells per microgel.

Advantageously, the viscosity of the hydrogel can decrease with increasing shear and/or strain on the hydrogel and increase or recover with decreased shear and/or strain. The the increased shear and strain can be associated with extruding or printing the hydrogel, and the viscosity of the hydrogel can recover after extruding or printing the hydrogel to provide the hydrogel with a defined shape, allowing the hydrogel and hence the composition to be utilized as a bioink, which can be printed through a needle or nozzle. For example, the hydrogel can have a storage modulus (G') higher than the loss modulus (G") with decreased shear and/or strain on the hydrogel and a loss modulus (G") higher than a storage modulus (G') with increased shear and strain on the hydrogel.

The cell-laden hydrogel so formed can be compatible with dispensing/printing while also having the ability of having cells remain viable and functional for several days/weeks/months during a biopreservation process. The cell-laden hydrogel comprise cells that maintain high viability and functionality after extended storage. By viability it is meant that after preservation or storage of the hydrogel, the cells are alive and capable of the same cell functions in existence prior to storage. In some cases, high viability means that at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% of the initial cell population is capable of survival, growth, and function after preservation or storage.

Cell viability can be determined using methods known in the art. A viability assay is an assay to determine the ability of organs, cells or tissues to maintain or recover viability. Viability can be distinguished from the all-or-nothing states of life and death by use of a quantifiable index between 0 and 1 (or 0 and 100%) (Pegg D E (1989). "Viability assays for preserved cells, tissues, and organs". Cryobiology 26(3): 212-231). For example, examining the ratio of potassium to sodium in cells can serve as an index of viability. If the cells do not have high intracellular potassium and low intracellular sodium, then the cell membrane may not be intact, and/or (2) the sodium-potassium pump may not be operating well. Thus, many assays that measure cell membrane integrity are used as quantitative measures of viability. These can be Trypan Blue, propidium iodide (PI), which are dyes that can penetrate leaky cell membranes and have been automated in commercially available cell counters. Other types of assays measure the overall metabolic rate of cell populations such as measuring total ATP, formazan-based assays (MTT/XTT) and Alomar blue-based or Resazurin-based assays. However quantitative measures of physiological function do not indicate whether damage repair and recovery is possible.

In other embodiments, the cell-laden hydrogel, microgels, and/or a composition that includes the cell-laden hydrogel and/or microgels can further include a bioactive agent that is capable of modulating a function and/or characteristic of a cell. For example, the bioactive agent may be capable of modulating a function and/or characteristic of a cell that is dispersed on or within the hydrogel and/or microgel. Alternatively or additionally, the bioactive agent may be capable of modulating a function and/or characteristic of an endogenous cell surrounding a hydrogel and/or microgel or structure formed from the hydrogel and/or microgel implanted in a tissue defect, for example, and guide the cell into the defect.

The at least one bioactive agent can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparin sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

In other embodiments, a composition comprising the cell-laden hydrogel and/or microgels can further include a cryopreservation and/or biopreservation agent. The composition including the cryopreservation and/or biopreservative agent and the cell-laden hydrogel and/or microgels can be cryopreserved, and the cryopreserved cells can have a substantially equivalent viability and functionality upon thawing compared to similar cells not cryopreserved. The cryopreservation and/or biopreservation agent can be provided in the composition at an amount effective to maintain a cell viability of at least about 70%, at least about 80%, or at least about 90% during and after cryopreservation. For example, the composition can include an amount of cryopreservation agent, such as Dimethyl sulfoxide (DMSO), effective to retain the viability of the cells after being stored for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 months at −10 to −80° C., such as −20° C.

Examples of cryopreservation agents include dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, inorganic salts, or any combination thereof. In some cases, the cryopreservation agent contains CryoStorCS2, CS5, or CS10 freeze media (BioLife Solutions, Inc) and 5% DMSO. In some cases, the cryopreservation agent contains between 1% and 15% DMSO, such as 2% to 7.5%, including 5% DMSO.

In some embodiments, the cell-laden hydrogel and/or microgels can be crosslinked with a second agent to form dual crosslinked hydrogel and/or microgels that have a free-standing structure with defined shape. In some embodiments, a plurality of second crosslink networks can be formed by crosslinking acrylate and/or methacrylate groups of the acrylated or methacrylated natural polymer macromer. The second crosslinking networks formed by crosslinking the acrylate groups or methacrylate groups of the acrylated and/or methacrylated natural polymer macromer can provide improved mechanical properties, such as resistance to shear or tensile loading and excessive swelling, as well as delayed biodegradation rate. For example, the storage modulus of the hydrogels can be strongly enhanced by secondary crosslinking. Since tissue constructs may be exposed to mechanical stresses (i.e., shear and tensile stresses) in in vivo environments, the increased mechanical properties of the hydrogel and/or microgels following secondary crosslinking may contribute to improving their stability when used in such applications.

In some embodiments, the acrylate or methacrylate groups of the acrylated and/or methacrylated natural polymer macromer of the hydrogel can be crosslinked by photocrosslinking using UV light in the presence of photoinitiators. For example, acrylated and/or methacrylated natural polymer macromers of the microgel can be photocrosslinked in an appropriate amount of diH$_2$O or aqueous media (e.g., PBS) containing a desired amount of a photoinitiator.

The hydrogel and/or microgels can be exposed to a light source at a wavelength and for a time to promote crosslinking of the acrylate groups of the polymers and form the photocrosslinked biodegradable hydrogel.

A photoinitiator can include any photo-initiator that can initiate or induce polymerization of the acrylate or methacrylate macromer. Examples of the photoinitiator can include camphorquinone, benzoin methyl ether, 2-hydroxy-2-methyl-1-phenyl-1-propanone, diphenyl(2,4,6-trimethyl-benzoyl)phosphine oxide, benzoin ethyl ether, benzophenone, 9,10-anthraquinone, ethyl-4-N,N-dimethylaminobenzoate, diphenyliodonium chloride and derivatives thereof.

In some embodiments, the cell-laden hydrogel and/or microgels can be crosslinked with the second crosslinking agent after dispensing the cell laden hydrogel and/or microgels from a dispensing device into a defined shaped. Prior to dispensing, the cell-laden microgels can be stored, for example, in a traditional screw or septum top bottle, or within a sterile closed-system device that can be removed from frozen- or non-frozen-storage and integrated with the dispensing device. The dispensing device can, for example, be a bioprinter or an automated or automated or manual injection device. Optionally, the bioprinter can be a three dimensional (3D) bioprinter.

In some embodiments, a composition that includes the cell-laden hydrogel and/or microgels can be used as a bioink for use in bioprinting. The bio-ink can include a composition comprising the cell-laden hydrogel and/or microgels. In some embodiments, the bioink additionally comprises non-cellular materials that provide specific biomechanical properties that enable bioprinting.

As used herein, "bioprinting" means utilizing three-dimensional, precise deposition of the cell-laden microgels via methodology that is compatible with an automated, computer-aided, three-dimensional prototyping device (e.g., a bioprinter).

In some embodiments, a bioprinter dispenses bioink comprising the cell-laden hydrogel and/or microgels from the cartridge in a specific pattern and at specific positions as directed by a computer aided design software in order to form a specific cellular construct, tissue, or organ. In order to fabricate complex tissue constructs, the bioprinter deposits the bioink at precise speeds and in uniform amounts. In some embodiments, a cartridge containing the bioink comprises one dispensing orifice. In various other embodiments, a cartridge comprises 2, 3, 4, 5, 6, 7, 8, 9, 10, 11, 12, 13, 14, 15, 20, 30, 40, 50, 60, 70, 80, 90, 100, or more dispensing orifices. In further embodiment, the edges of a dispensing orifice are smooth or substantially smooth.

Many types of cartridges are suitable for use with bioprinters. In some embodiments, a cartridge is compatible with bioprinting that involves extruding the bioink, which includes the cell-laden hydrogel and/or microgels, through one or more dispensing orifices. In some embodiments, a cartridge is compatible with non-continuous bioprinting. In some embodiments, a cartridge is compatible with continuous and/or substantially continuous bioprinting.

In some embodiments, a cartridge is a capillary tube or a micropipette. In some embodiments, a cartridge is a syringe or a needle. Many internal diameters are suitable for substantially round or cylindrical cartridges. In various embodiments, suitable internal diameters include, by way of non-limiting examples, 1, 10, 50, 100, 200, 300, 400, 500, 600, 700, 800, 900, 1000 or more μm, including increments therein.

In some embodiments, a cartridge has an internal diameter of about 1 μm to about 1000 μm. In a particular embodiment, a cartridge has an internal diameter of about 500 μm. In another particular embodiment, a cartridge has an internal diameter of about 250 μm. Many internal volumes are suitable for the cartridges disclosed herein. In various embodiments, suitable internal volumes include, by way of non-limiting examples, 0.1, 1, 10, 20, 30, 40, 50, 100, 200, 300, 400, 500, 600, 700, 800, 900, 1000 or more ml, including increments therein. In other various embodiments, suitable internal volumes include, by way of non-limiting examples, 1, 2, 3, 4, 5, 10, 20, 30, 40, 50, 60, 70, 80, 90, 100, 199, 300, 400, 500 or more ml, including increments therein.

In some embodiments, the cartridge is compatible with ink-jet printing of bioink and/or support material onto a receiving 2D or 3D surface. In some embodiments, the bioink can printed into a stabilizing bath/gel that is effective to maintain the shape of the printed bioink. Examples of stabilizing baths or gels include those used in freeform reversible embedding of suspended hydrogels (FRESH) 3D bioprinting techniques.

The bioink once printed into a defined shape using, for example, a 3D printer can be crosslinked with the second crosslinking agent to mechanically stabilize the printed construct such that it forms a free-standing structure. The stabilizing gel can be removed after crosslinking the bioink with the second crosslinking agent to allow removal of the construct so formed.

In some embodiments, a construct and/or tissue construct so formed from the crosslinked bioink can be used to promote tissue growth in a subject. For example, a target site for the tissue construct can be identified in a subject in need thereof. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

In some embodiments, the tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed ACI or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, the tissue construct formed from the composition or bioink described herein having a desired shape can be administered to the target site. The tissue construct can be prepared according to the method described above.

The following example is for the purpose of illustration only and is not intended to limit the scope of the claims, which are appended hereto.

EXAMPLE 1

In this example, we have fabricated oxidized methactrylated alginate (OMA) microgels and explored their potential as building blocks for bottom-up assembly via manual assembly and 3D printing for tissue engineering applications. OMA droplets can be ionically-crosslinked into microgels with the addition of calcium ions, and then assembled together into a bulk hydrogel by photocrosslinking under low-level ultraviolet (UV) light. Using these principles, we heterogeneously assembled the OMA microgels and scaled them up into large, defined, and complex biological structures using the freeform reversible embedding of suspended hydrogels (FRESH) 3D bioprinting technique.

Figure 6A:
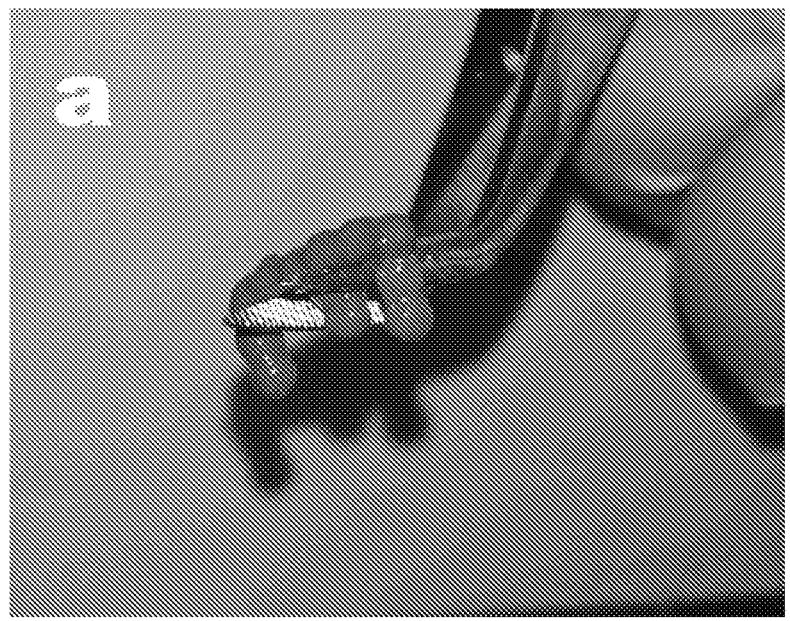
FIGS. 6A-C illustrate 3D assembled magnetic hydrogel bead structures. (A) Magnetic OMA beads were manually arranged to form the letter E and then stabilized under UV light (20 mW/cm$^2$ for 1 min). The resulting assembly could be lifted up with a tweezer. Magnetic OMA beads were collected using a permanent magnet to form (B dome and (C) tube shapes and then crosslinked together under UV light (20 mW/cm$^2$ for 1 min).
Figure 6B:
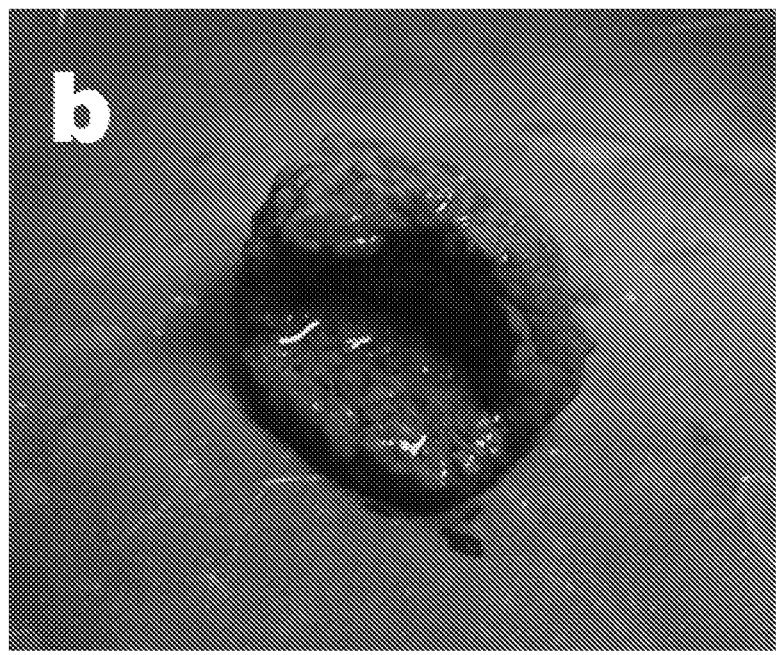
Figure 6C:
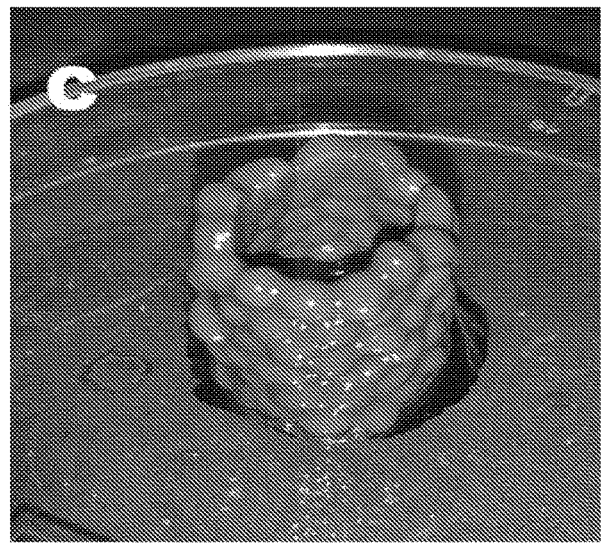

To evaluate the feasibility of easy assembly of OMA microgels, we first fabricated OMA hydrogel beads since the OMA beads are rather easy to handle and manually assemble than the microgels. Fabrication of OMA hydrogel beads was performed by extruding OMA macromer solution through a needle to form OMA droplets into a calcium chloride gelling bath [FIG. 1A(i)]. OMA droplets immediately reacted with $Ca^{2+}$ to form ionically-crosslinked OMA beads [FIG. 1A(ii)]. After manually connecting individual OMA beads on a glass plate [FIG. 1B(i)], structures of physically linked OMA beads were fabricated through the application of UV irradiation [FIG. 1B(ii)]. Since the ionically crosslinked OMA beads have methacrylated groups, crosslinks formed under UV light between the OMA bead units to stabilize the resulting assembly [FIG. 1B(iii)]. While OMA beads joined together via photocrosslinking could be lifted up from the glass plate as a stand-alone assembled construct [FIG. 1B(v)], individual OMA beads detached from a non-UV irradiated OMA bead assembly [FIG. 1B(vi)]. To evaluate the capability of a magnetic assembly approach, which is a robust and facile method to assemble small particles and fabricate various structures, magnetic OMA beads were prepared. As shown in FIG. 6, magnetic OMA beads could be assembled into letter, dome, and tube shapes. Although this approach offers simple and rapid assembly of magnetic OMA beads, there is still limited control over the formation of complex, 3D biological structures.

Since smaller microgels (diameter<300 μm) can enhance mass transport to/from encapsulated cells to achieve a more efficient nutrient and waste exchange due to larger surface-to-volume ratio, alginate beads (diameter>1 mm) formed by the simple dripping method are not ideal for cell encapsulation. Therefore, a coaxial airflow-induced microgel generator was designed [FIG. 2A(i)] that could fabricate microgels (diameter<300 μm) with encapsulated human bone marrow-derived mesenchymal stem cell (hMSC) [FIG. 2A(ii)]. High cell viability was observed after cell encapsulation (FIG. 2b), indicating that the macromer solution, coaxial flow, and ionic crosslinking (0.2 M $CaCl_2$) encapsulation process were non-toxic to the cells. Microgel encapsulated hMSCs also maintained high cell viability after 4 weeks of spinner flask culture [FIG. 2C(i)]. Furthermore, these cell-laden microgels could be directly assembled while maintaining high cell viability [FIG. 2C(ii)].

Figure 3A:
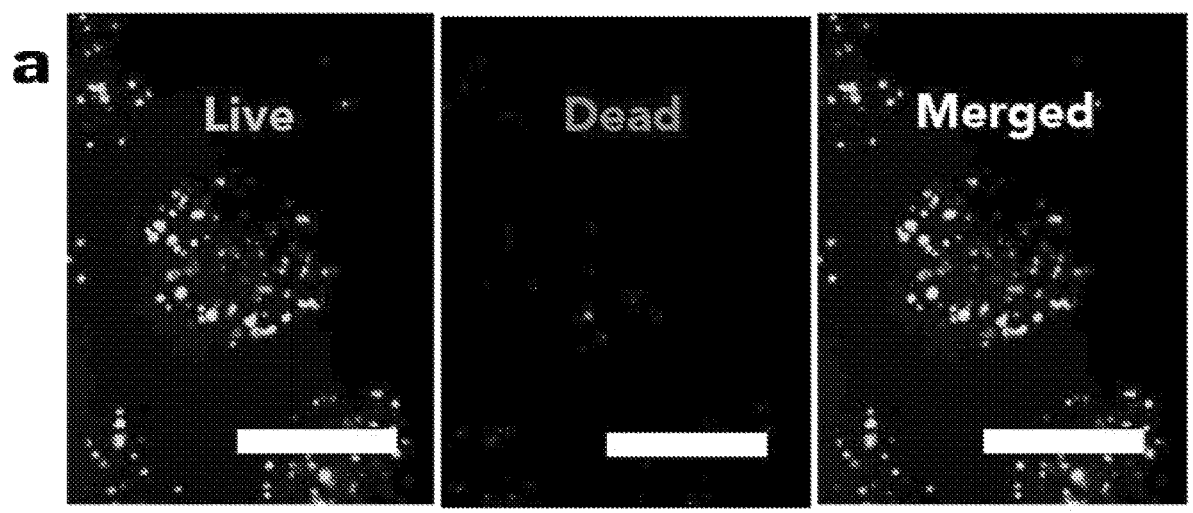
FIGS. 3A-E illustrate Cryopreservation of hMSC-laden OMA microgels. (A) Live/Dead images of cryopreserved hMSC-laden OMA microgels after recovery from cryopreservation in liquid nitrogen. Green color indicates vital cells and red color indicates dead cells. (B) Quantification of DNA in the hMSC-laden OMA microgels after 2 and 4-week culture in growth media. (C) Osteogenic differentiation of cryopreserved hMSC-laden OMA microgels for 4 weeks. Quantification of i) ALP activity and ii) mineralization normalized by DNA, and Alizarin red S staining of iii) freshly made and iv) cryopreserved hMSC-laden OMA microgels demonstrated no significant differences between cryopreserved and fresh microgels. (D) Chondrogenic differentiation of cryopreserved hMSC-laden OMA microgels for 4 weeks. i) Quantification of GAG content normalized DNA and Alcian blue staining of ii) freshly made and iii) cryopreserved hMSC-laden OMA microgels also demonstrated no significant differences between cryopreserved and fresh microgels. (E) Heterogeneously assembled osteogenically (red) and chondrogenically (green) differentiated hMSC-laden OMA microgels structures. i) Osteogenically differentiated hMSC-laden OMA microgels were assembled around a chondrogenically differentiated hMSC-laden OMA microgel. ii) Chondrogenically differentiated hMSC-laden OMA microgels were assembled around an osteogenically differentiated hMSC-laden OMA microgel. iii) Osteogenically differentiated hMSC-laden OMA microgel layer was assembled between chondrogenically differentiated hMSC-laden OMA microgel layers. iv) Two of chondrogenically differentiated hMSC-laden OMA microgels were connected. Subsequently, osteogenically differentiated hMSC-laden OMA microgels were attached to the assembly. The scale bars indicate 200 μm.

Since preservation and "off-the-shelf" availability of biotherapeutics may be valuable for their clinical translation, cryopreservation has been extensively studied as a viable solution to the long-term storage of cells, tissues, and embryos. The development of effective, safe, and sterile cryopreservation protocols is a prerequisite for the long-term storage of these biologics. Dimethyl sulfoxide (DMSO) is one of the most commonly used cryoprotectants to aid in the long-term storage of viable biologics due to its ability to penetrate the cell membrane and reduce the formation of ice crystals during the freezing process. As 10% DMSO has been shown to not adversely affect hMSCs' viability and proliferative capacities, in this study, a mixture of 10% DMSO and 90% growth media (DMEM with 10% FBS, 1% P/S and 10 ng/ml FGF-2) was used as a cryopreservation solution for microgel encapsulated hMSCs hMSC-laden microgels. The cryopreserved microgels with encapsulated hMSCs thawed rapidly during the recovery process, and the viability of recovered hMSCs was examined using a live/dead assay. hMSCs exhibited high cell viability after recovery from cryopreservation in liquid nitrogen (FIG. 3A).

Figure 3B:
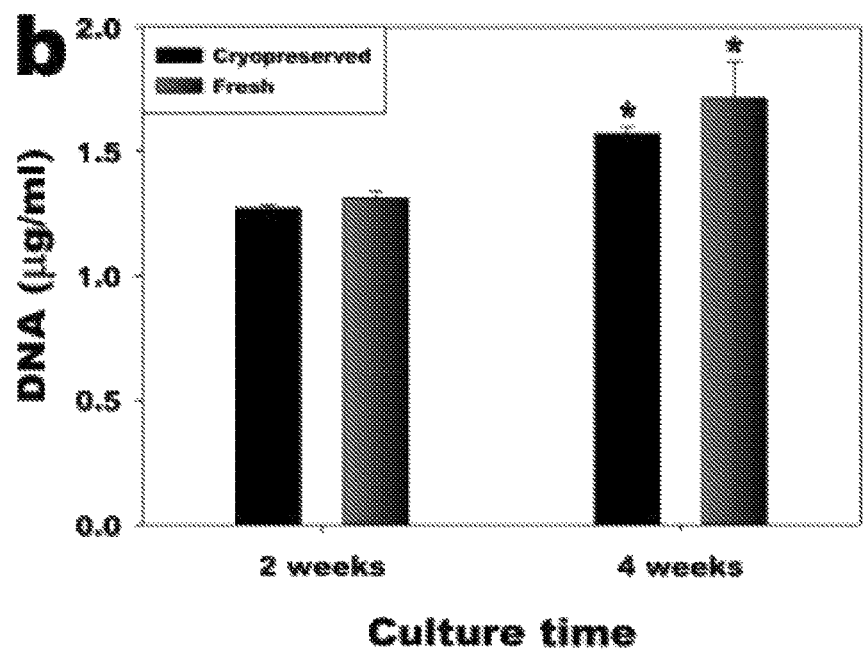
Figure 3C:
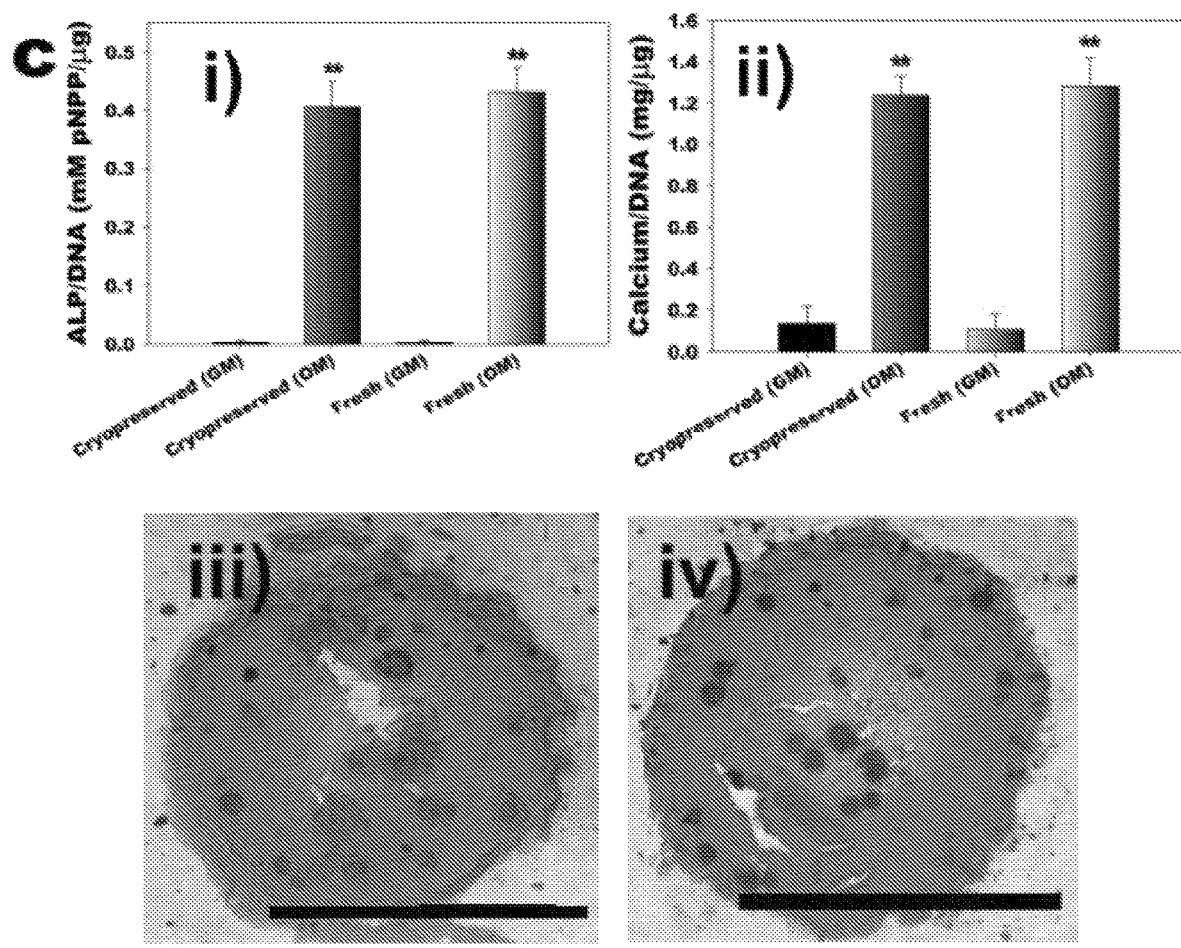
Figure 3D:
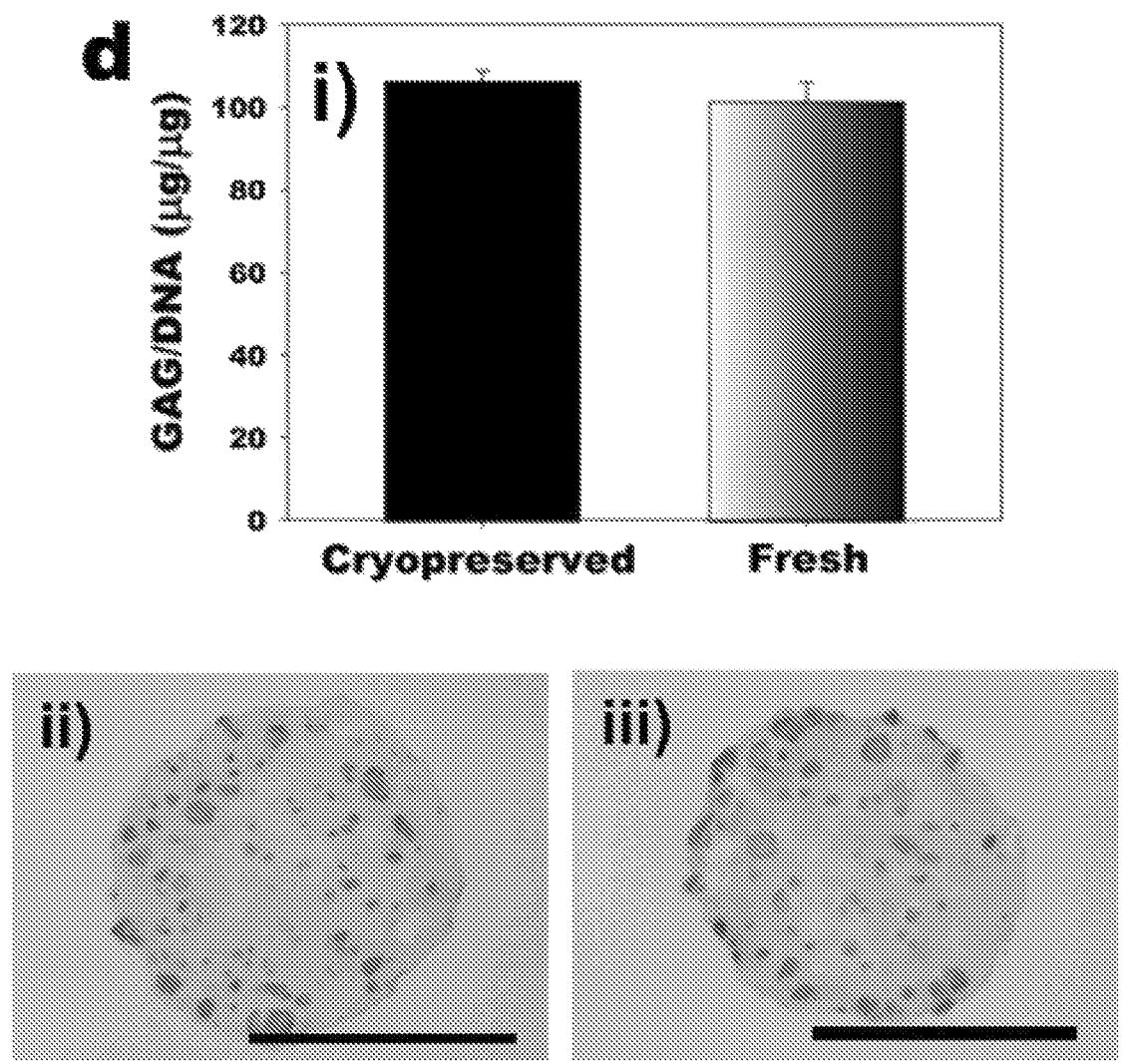
Figure 3E:
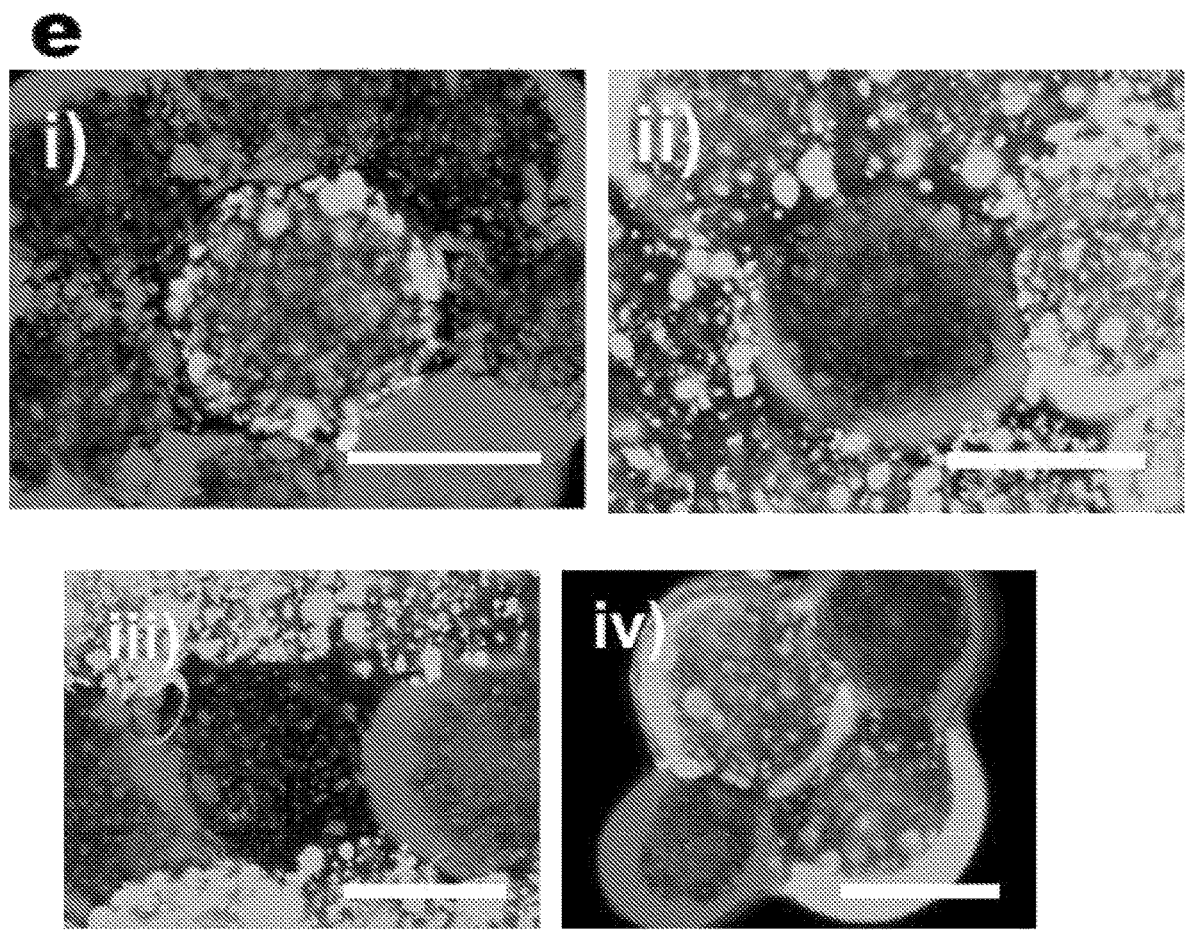
Figure 7A:
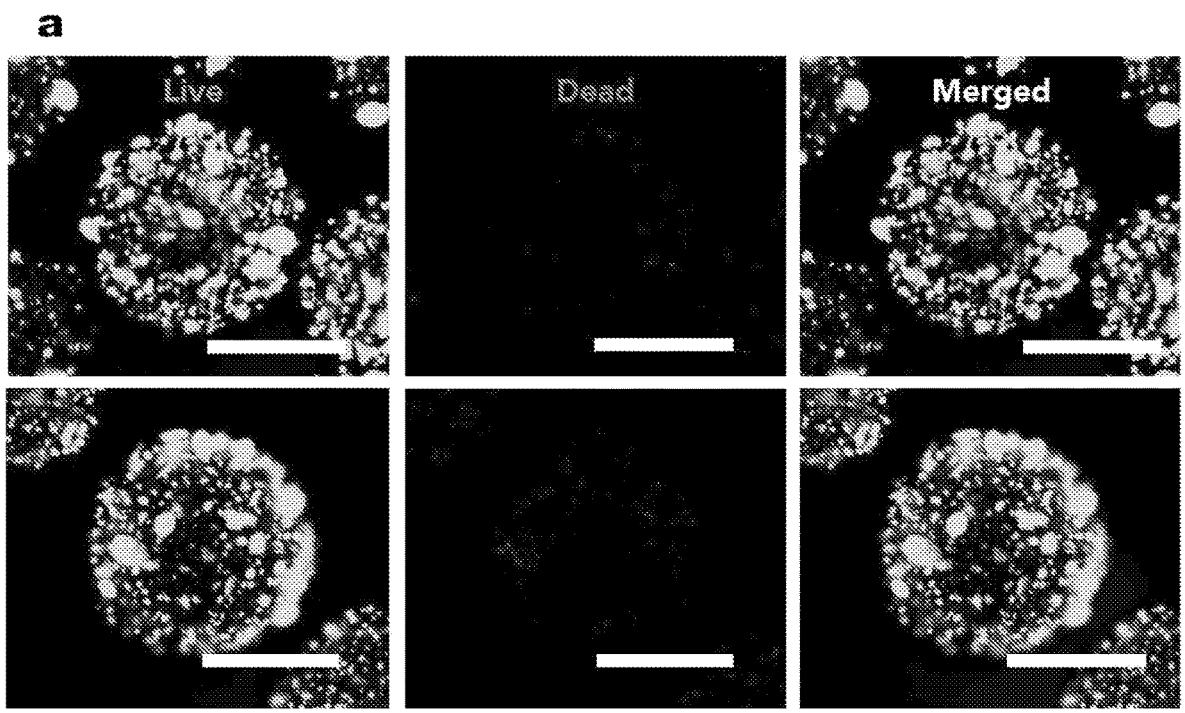
FIGS. 7A-B illustrate four weeks chondrogenic differentiation of cryopreserved hMSC-laden OMA microgels. (A) Live/Dead staining of encapsulated hMSCs in OMA microgels (top row: freshly made microgel, bottom row: cryopreserved microgel). Green color indicates vital cells and red color indicates dead cells. (B) Toluidine blue O staining of freshly made (left) and cryopreserved (right) hMSC-laden OMA microgels demonstrated no significant difference between cryopreserved and fresh microgels.
Figure 7B:
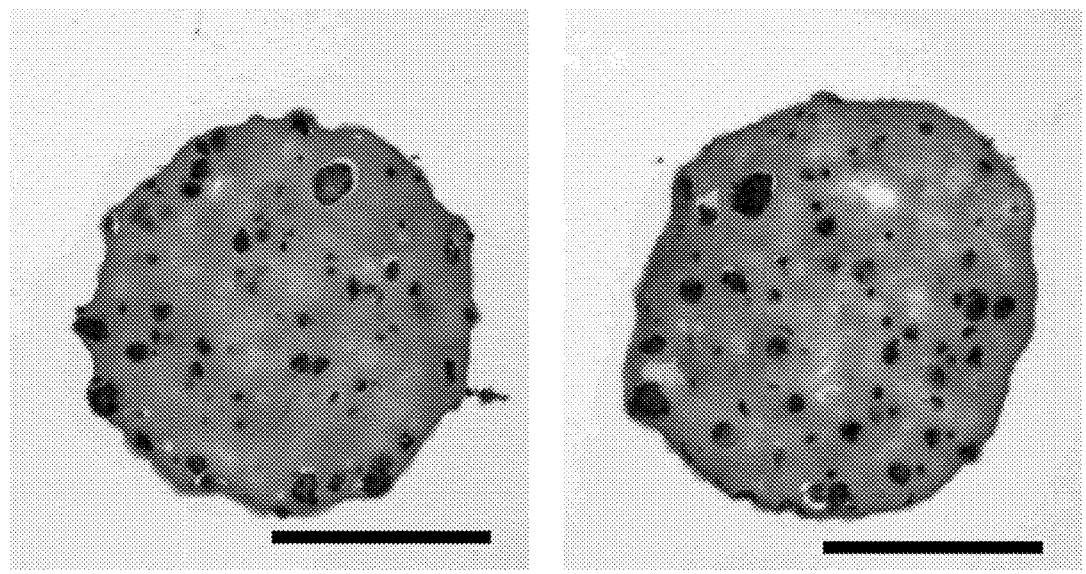

Since cryopreservation has been known to affect the function of stem cells, the proliferative capacities and differentiation potentials of hMSC-laden microgels derived from cryopreserved or freshly prepared microgels were compared. To indirectly examine the change in the number of hMSCs encapsulated within the microgels, DNA content was measured over a period of 4-week culture in growth media (FIG. 3B). The DNA content of both microgel groups significantly increased over the 4 weeks. However, there was no significant difference in DNA content between the two groups. To investigate the effect of microgel cryopreservation on the differentiation behavior of the stem cells, hMSC-laden microgels derived from cryopreserved or freshly prepared microgels were cultured in osteogenic differentiation media for 4 weeks. Osteogenesis of hMSCs was evaluated by measuring alkaline phosphatase (ALP) activity and quantifying calcium deposition by staining with Alizarin red S (FIG. 3C). ALP activity of encapsulated hMSCs in microgels and mineralization of the microgels were significantly increased by culturing in osteogenic differentiation media, compared to growth media [FIG. 3C(i,ii)]. However, there was no significant difference in ALP activity [FIG. 3C(i)] or mineralization [FIG. 3C(ii-iv)] between cryopreserved and fresh microgels. hMSC-laden microgels derived from cryopreserved or freshly prepared microgels were also cultured in chondrogenic differentiation media for 4 weeks to evaluate the effect of cryopreservation on chondrogenesis of hMSCs encapsulated in microgels. The cell viability of hMSCs in previously cryopreserved microgels was observed to be at similar level as in fresh microgels after chondrogenic differentiation (FIG. 8A). Chondrogenesis of hMSCs was evaluated by quantifying glycosaminoglycan (GAG) content [FIG. 3D(i)] and staining with Alcian blue [FIG. 3D(ii-iii)] and Toluidine blue O (FIG. 7B). Similar to the osteogenic differentiation findings, there was no significant difference in GAG/DNA between cryopreserved and fresh microgels [FIG. 3D(i)]. Similar levels of Alcian blue and Toluidine blue O staining was also observed in the cryopreserved hMSC-laden microgels and fresh microgels. The formation of cell clusters was observed throughout both groups, further indicating chondrogenic differentiation. These results clearly demonstrate that the differentiation potential of hMSC-laden microgels toward the osteogenic and chondrogenic pathways was maintained even after cryopreservation. Thus, these cryopreserved hMSCs encapsulated in microgels with preserved proliferation and differentiation capabilities could be valuable for tissue regeneration and cell-based therapies. To visualize the OMA microgels, osteogenically- and chondrogenically-differentiated microgels were labeled with red and green fluorescent dyes, manually heterogeneously assembled, successfully stabilized by photocrosslinking under UV, and imaged (FIG. 3E).

Figure 4A:
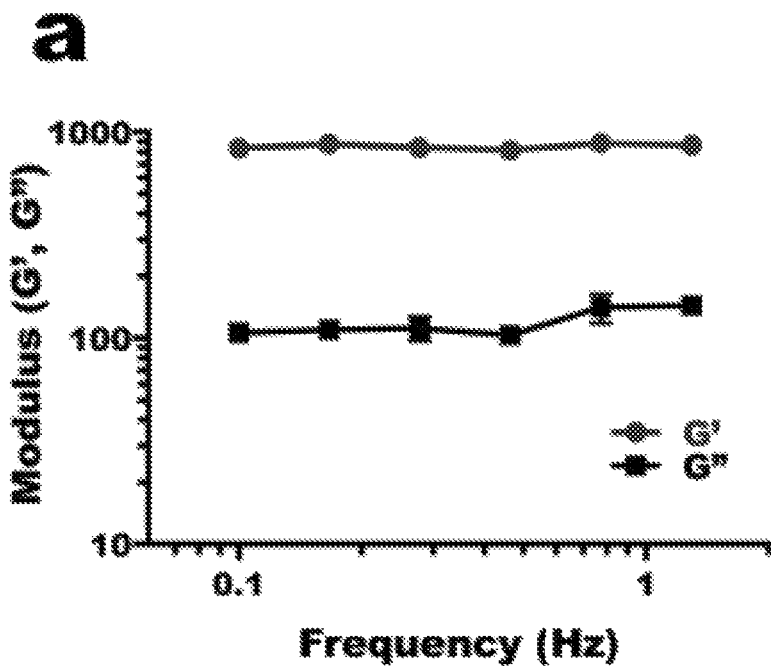
FIG. 4A-F illustrate shear-thinning and self-healing properties of the OMA microgels. A) Storage (G') and loss (G") moduli of hMSC-laden OMA microgels as a function of frequency. G' is larger than G" over the measured frequency range and both exhibited frequency independence. Viscosity of hMSC-laden OMA microgels as a function of (B) shear rate and (C) shear strain demonstrates the shear-thinning behavior of hMSC-laden OMA microgels. (D) G' and G" of hMSC-laden OMA microgels as a function of shear strain exhibits their shear-yielding behavior and gel-to-sol transition at higher shear strain. (E) Shear moduli and (F) viscosity changes by dynamic strain tests of hMSC-laden OMA microgels with alternating low (1%) and high (100%) strains at 1 Hz demonstrate rapid recovery of microgel bioink strength and viscosity within seconds, which indicates self-healing properties of hMSC-laden OMA microgels.
Figure 4B:
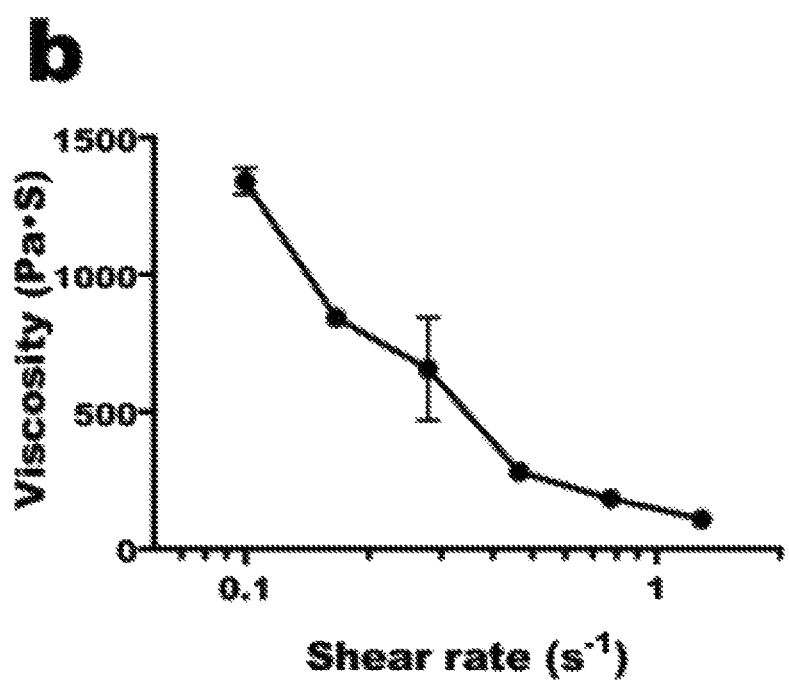
Figure 4C:
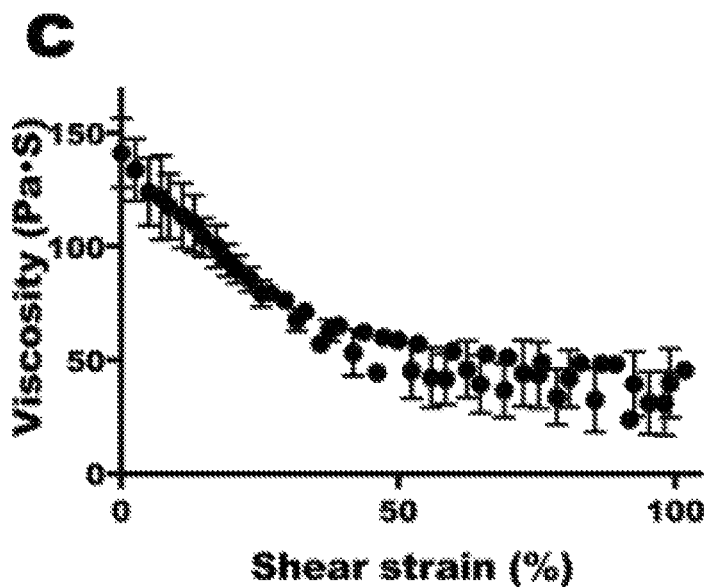
Figure 4D:
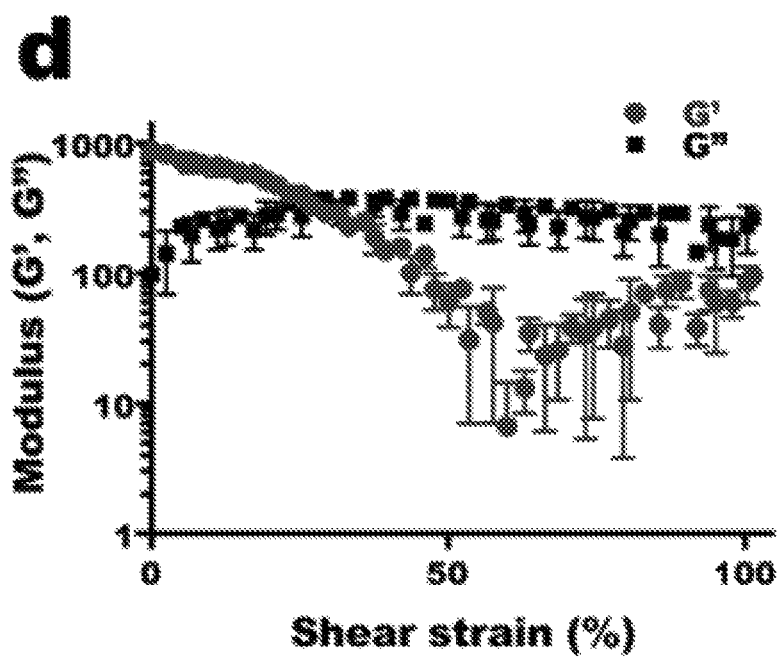
Figure 4E:
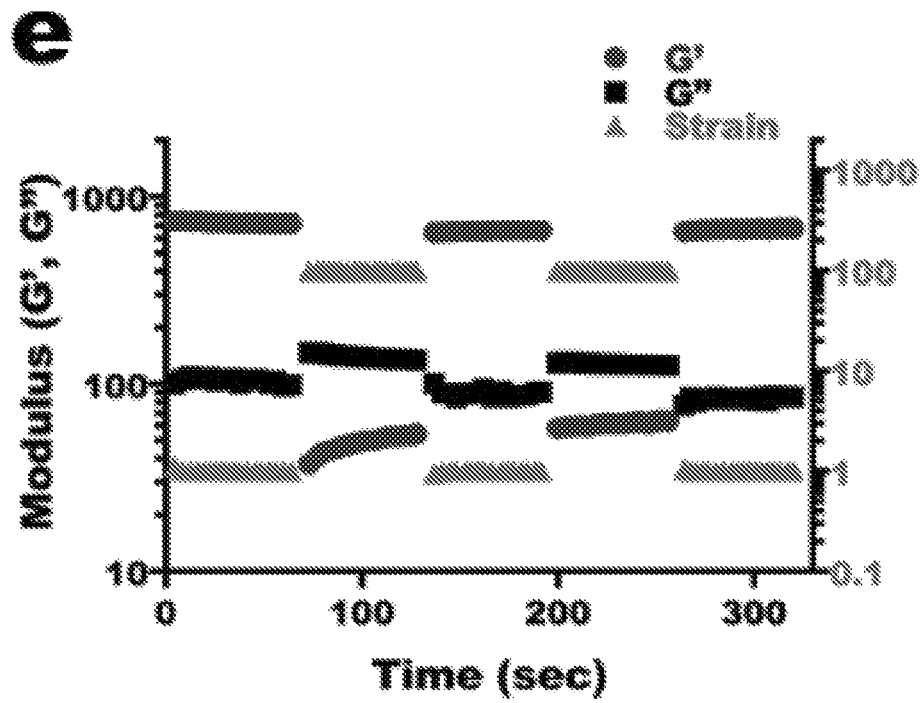
Figure 4F:
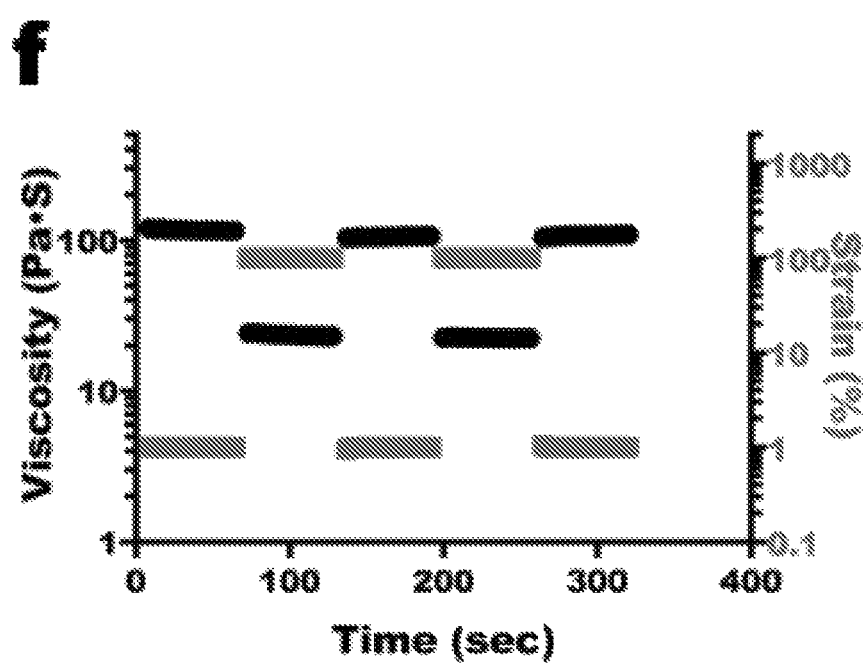

Shear-thinning and self-healing characteristics can enhance the 3D printing capacity of materials; therefore, we evaluated whether the hMSC-laden microgels exhibit these properties before utilizing them for 3D bioprinting. Frequency sweeps of hMSC-laden OMA microgels showed significantly higher G' than G", indicating that hMSC-laden OMA microgels were mechanically stable (FIG. 4A). From continuous flow experiments, we observed that the viscosity of hMSC-laden OMA microgel bioink decreased with increasing shear rate and shear strain, demonstrating shear-thinning characteristics (FIG. 4B-C). Moreover, G" surpassed G' at approximately 25% strain in an oscillatory strain sweep test, which is an indication of shear-yielding, an important property of hydrogel materials for injectability and/or printability through a needle (FIG. 4D). When investigated under the cyclic strain sweeps by alternating low (1%) and high (100%) strains, the hMSC-laden OMA microgel bioink went from solid-like to liquid-like behavior in response to strain (FIG. 4E). Furthermore, the responses of shear moduli (FIG. 4E) and viscosity (FIG. 4F) to high strain and recoveries at low strain were rapid and repeatable. The combination of shear-thinning and shear-yielding properties allows for the rapid transition from solid-like to liquid-like behavior, making the hMSC-laden OMA microgels well-suited for injection and extrusion-based 3D printing. The rapid recovery of mechanical properties after removal of shear force, as occurs after the deposition of bioinks, allows for stabilization of the printed bioinks immediately after extrusion.

Figure 5A:
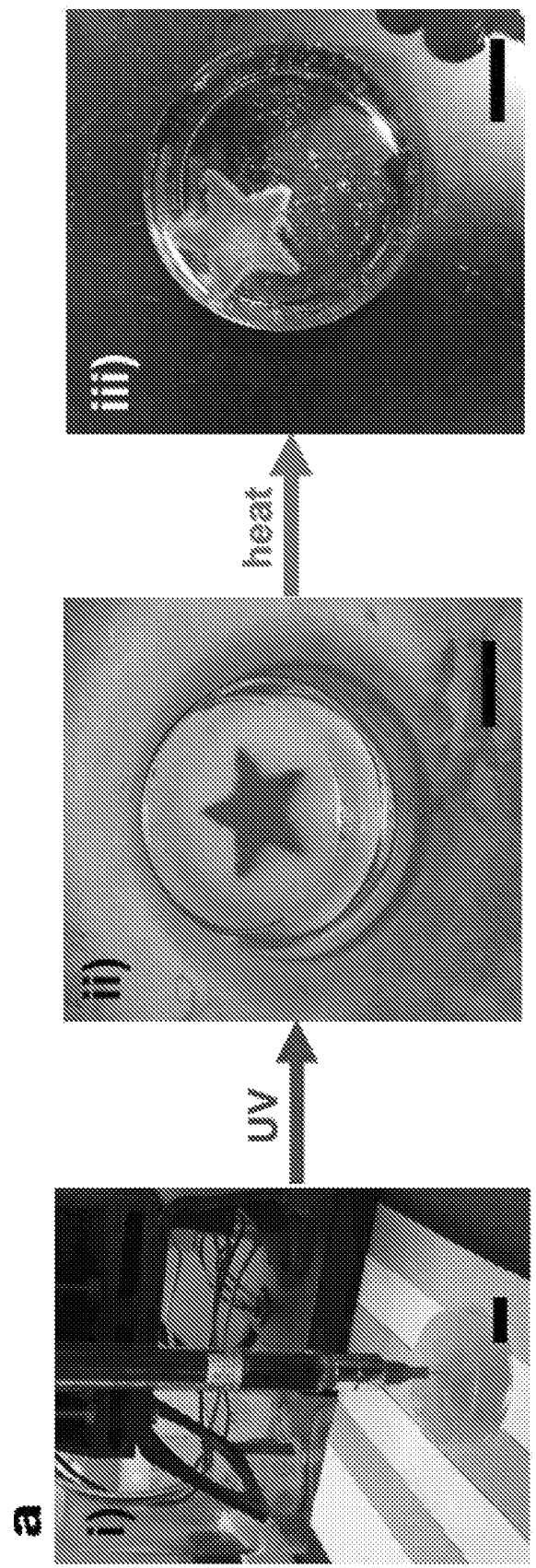
FIGS. 5A-E illustrate FRESH 3D printing of hMSC-laden OMA microgels. (A) i) FRESH 3D printing of Alizarin red S-stained hMSC-laden OMA microgels using a 3D printer modified with a custom syringe-based extruder; ii) Assembly of a 3D printed star-shaped structure by photocrosslinking; iii) heated release of the assembled structure from the gelatin slurry bath. To visualize the 3D printed structure, microgels were stained with Alizarin red S prior to printing. (B) i) FRESH 3D printed letters (CWRU) and ii) a Live/Dead image of an assembled 3D printed structure. Green color indicates vital cells and red color indicates dead cells. 3D printed (C) femur and (D) skull using Alizarin red S stained hMSC-laden OMA microgels after osteogenic differentiation, and (E) an ear using Toluidine blue O stained hMSC-laden OMA microgels after chondrogenic differentiation. i) s are digital images and ii)s are their 3D printed structures. The black scale bars and the white scale bar indicate 1 cm and 100 μm, respectively.
Figure 5B:
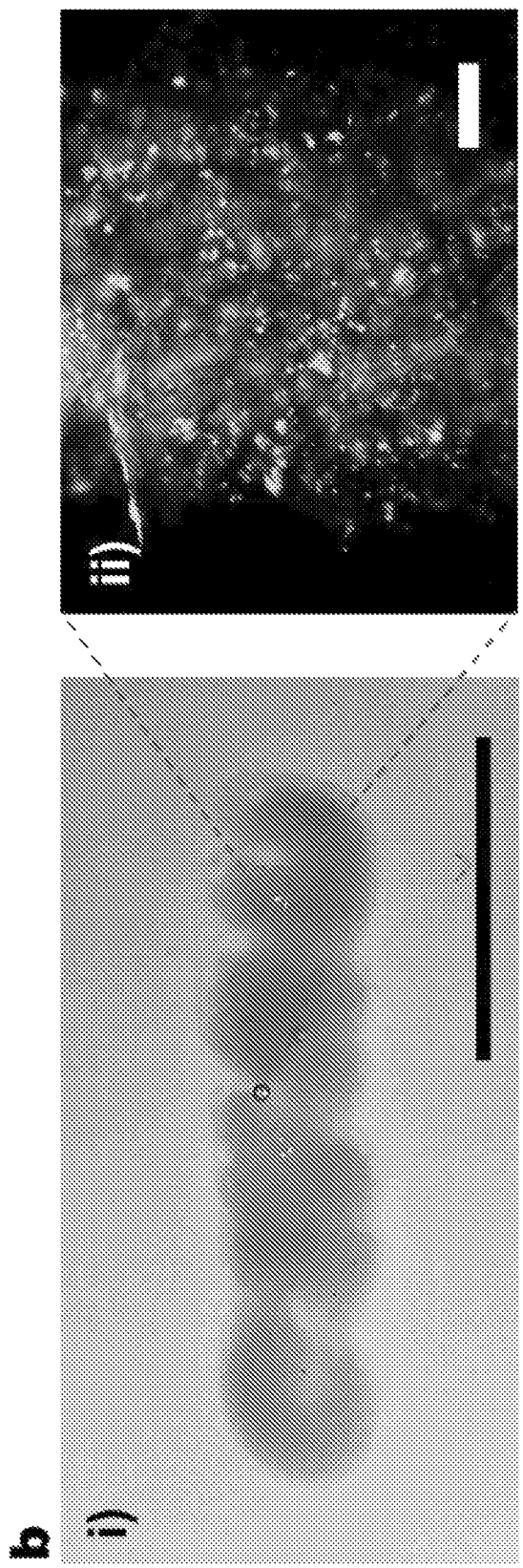
Figure 5C:
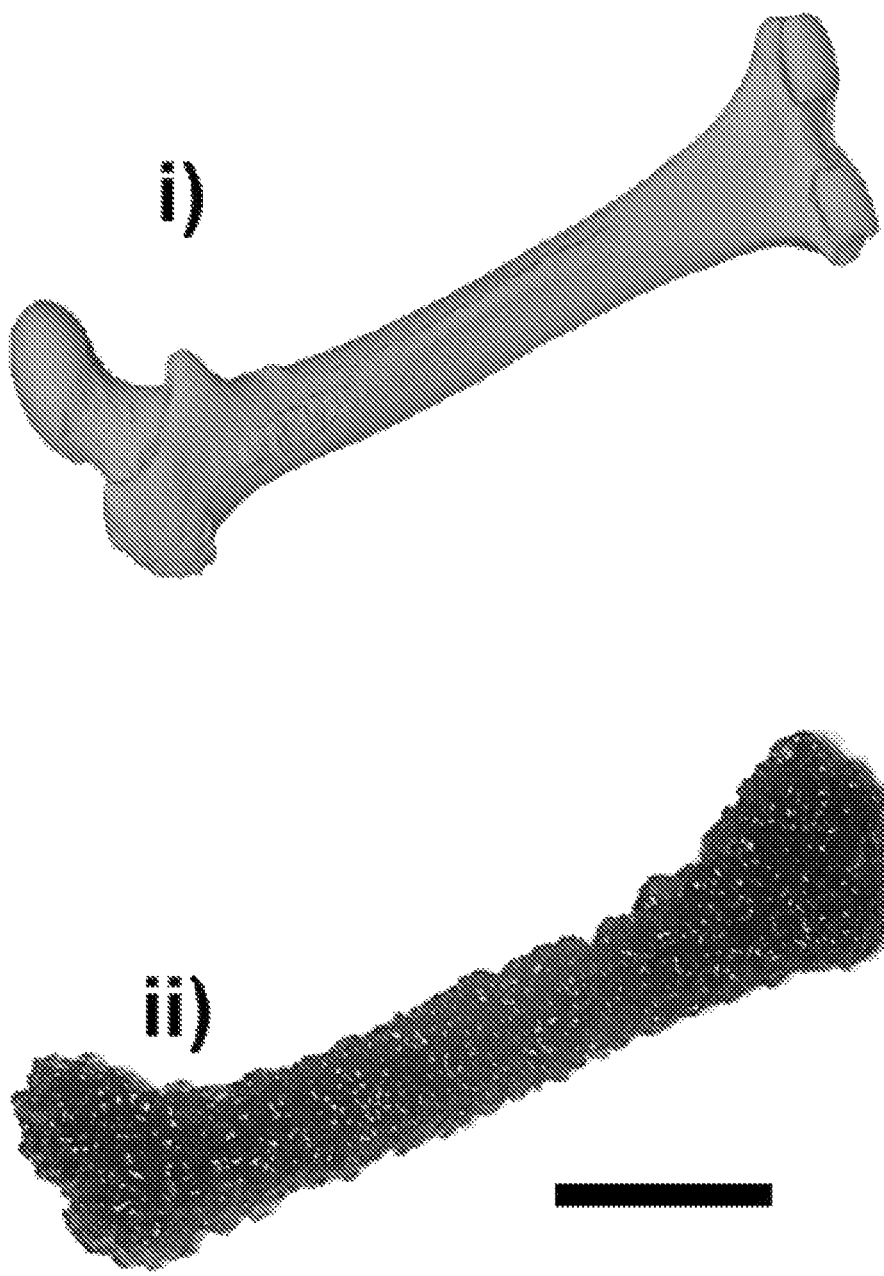
Figure 5D:
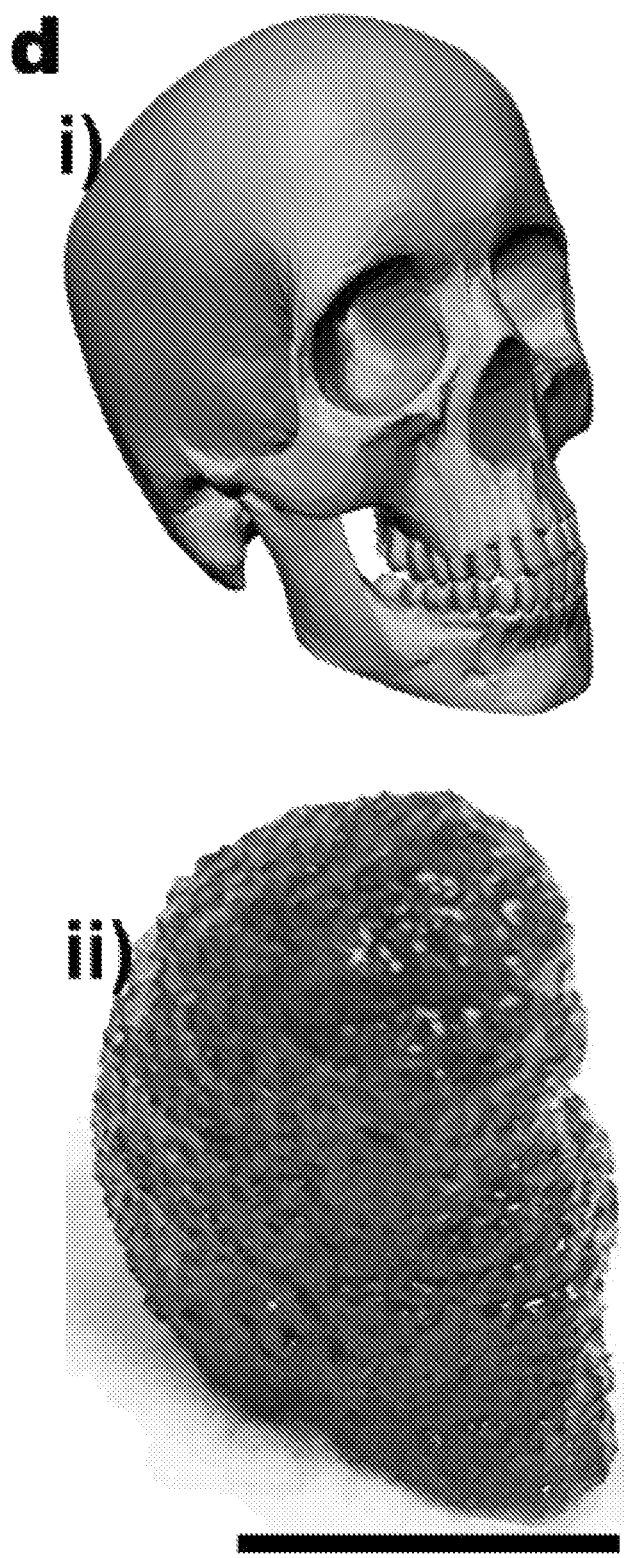
Figure 5E:
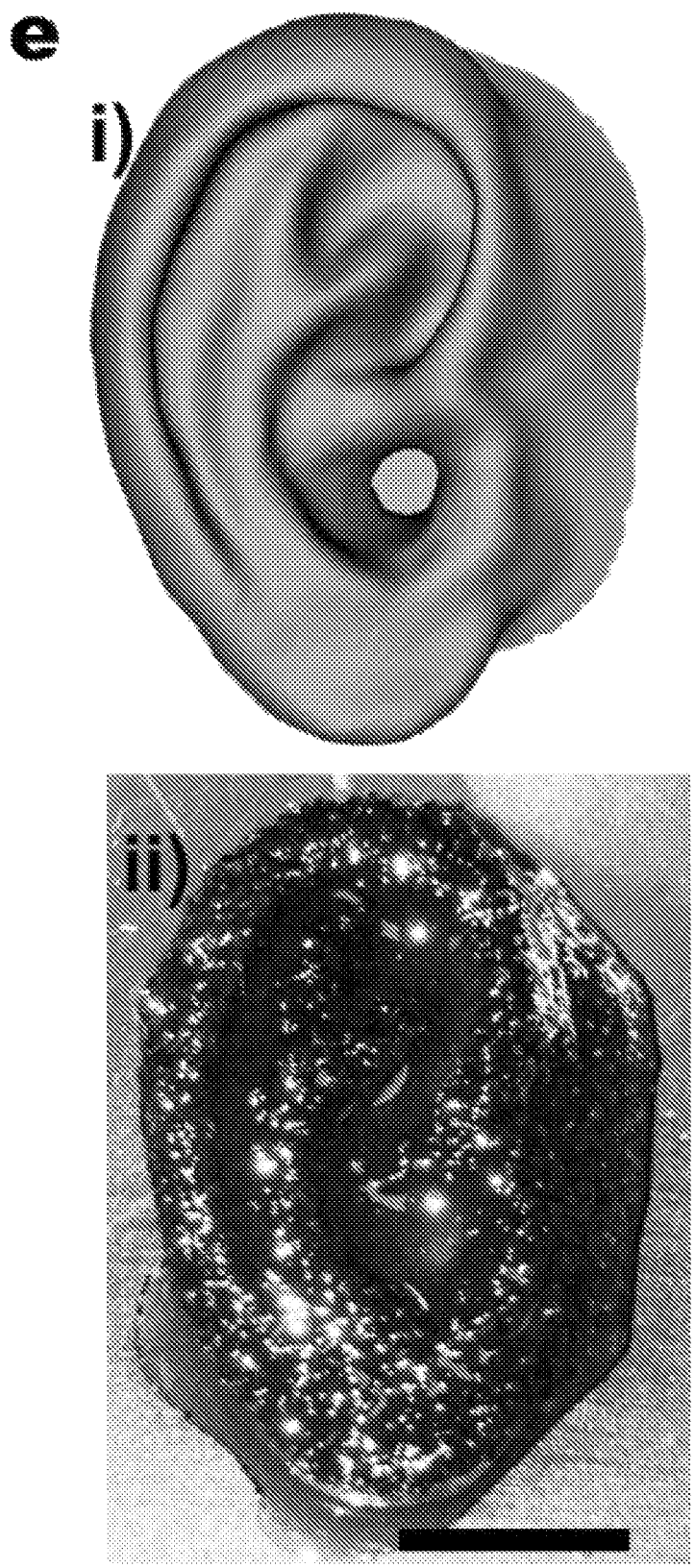
Figure 9C:
Figure 9D:
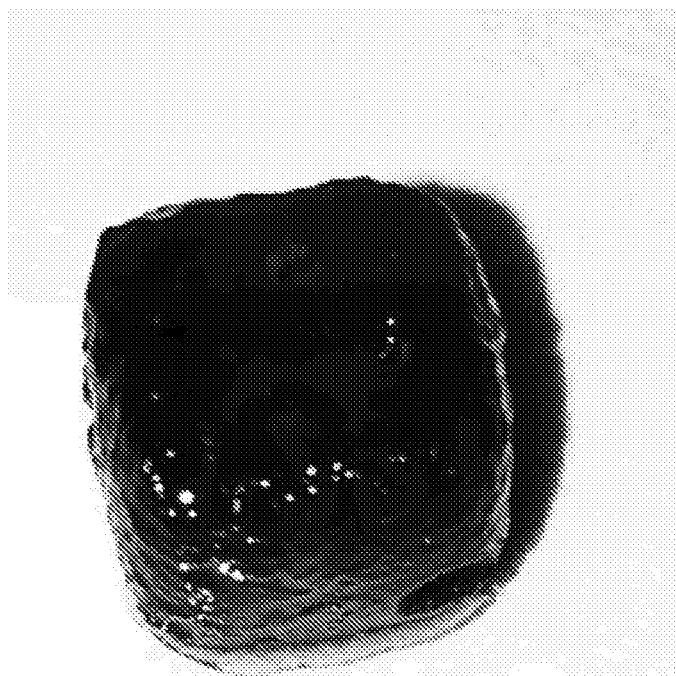

We formed complex 3D printed biological structures by assembly of the hMSC-laden OMA microgels using the FRESH 3D bioprinting technique. Here, we show that hMSC-laden microgel bioink could be FRESH printed by extrusion within the gelatin microparticle slurry support bath (FIG. 9B), which maintains the intended 3D printed structure during the printing process [FIG. 5A(i) and FIG. 9A]. After the entire 3D structure was printed, hMSC-laden microgels were crosslinked together under UV light [FIG. 5A(ii)]. By incubating the 3D printed structure at 37° C., the supporting gelatin bath could be easily removed in a non-destructive manner [FIG. 5A(iii)]. As shown in FIG. 5b (letters of CWRU), high cell viability was observed even after 3D printing and removal of the gelatin slurry, indicating the FRESH 3D printing of cryopreserved microgels is a cell-friendly process. To demonstrate construction of tissue constructs with complex shapes, a femur (FIG. 5C), a skull (FIG. 5D), an ear (FIG. 5E), letters (FIG. 9C) and a cube (FIG. 9D) were fabricated using 3D printing of the osteogenically or chondrogenically differentiated hMSC-laden microgels. Upon FRESH 3D bioprinting and assembly of Alizarin red S stained (femur and skull) and Toluidine blue O stained microgels (ear), it was demonstrated that stem cell-laden microgels differentiated down specific lineages could applied using this strategy to create biological complex structures.

In conclusion, hMSC-laden microgels have been fabricated using a dual-crosslinkable OMA hydrogel. The hMSC-laden OMA microgels were directly assembled into well-defined 3D shapes and structures under low-level UV light. hMSC-laden microgels were successfully cryopreserved for long-term storage, and the recovered hMSCs were equivalent in functionality to freshly processed stem cells. Finally, cell-laden OMA microgels could be applied as a unique bioink for FRESH bioprinting to create complex 3D tissue structures. The directed assembly and 3D printing of cell-laden microgels provide a powerful and highly scalable platform technology for biomimetic 3D tissue construction and presents a new paradigm for 3D bioprinting of microscale materials.

Methods

Synthesis of OMA

Oxidized alginate (OA) was prepared by reacting sodium alginate (Protanal LF 200S, FMC Biopolymer) with sodium periodate (Sigma) using a modification of a previously described method. Briefly, sodium alginate (10 g) was dissolved in ultrapure deionized water (diH$_2$O, 900 ml) overnight. Sodium periodate (0.1 g) was dissolved in 100 ml diH$_2$O, added to alginate solution under stirring to achieve 1% theoretical alginate oxidation, and allowed to react in the dark at room temperature for 24 hrs. The oxidized, methacrylated alginate (OMA) macromer was prepared by reacting OA with 2-aminoethyl methacrylate (AEMA, Sigma). To synthesize OMA, 2-morpholinoethanesulfonic acid (MES, 19.52 g, Sigma) and NaCl (17.53 g) were directly added to an OA solution (1 L) and the pH was adjusted to 6.5. N-hydroxysuccinimide (NHS, 1.176 g; Sigma) and 1-ethyl-3-(3-dimethylaminopropyl)-carbodiimide hydrochloride (EDC, 3.888 g; Sigma) (molar ratio of NHS:EDC=1:2) were added to the mixture under stirring to activate 20% of the carboxylic acid groups of the alginate. After 5 min, AEMA (1.688 g) (molar ratio of NHS:EDC:AEMA=1:2:1) was added to the product, and the reaction was maintained in the dark at RT for 24 hrs. The reaction mixture was precipitated with the addition of excess of acetone, dried in a fume hood, and rehydrated to a 1% w/v solution in diH$_2$O for further purification. The OMA was purified by dialysis against diH$_2$O (MWCO 3500; Spectrum Laboratories Inc.) for 3 days, treated with activated charcoal (5 g/L, 50-200 mesh, Fisher, Pittsburgh, Pa.) for 30 min, filtered (0.22 μm filter) and lyophilized To determine the levels of alginate oxidation and methacrylation, the OMA were dissolved in deuterium oxide (D$_2$O, 2 w/v %), and $^1$H-NMR spectra were recorded on a Varian Unity-300 (300 MHz) NMR spectrometer (Varian Inc.) using 3-(trimethylsilyl)propionic acid-d$_4$ sodium salt (0.05 w/v %) as an internal standard.[30]

Fabrication and Directed Assembly of OMA Hydrogel Beads

Figure 1B:
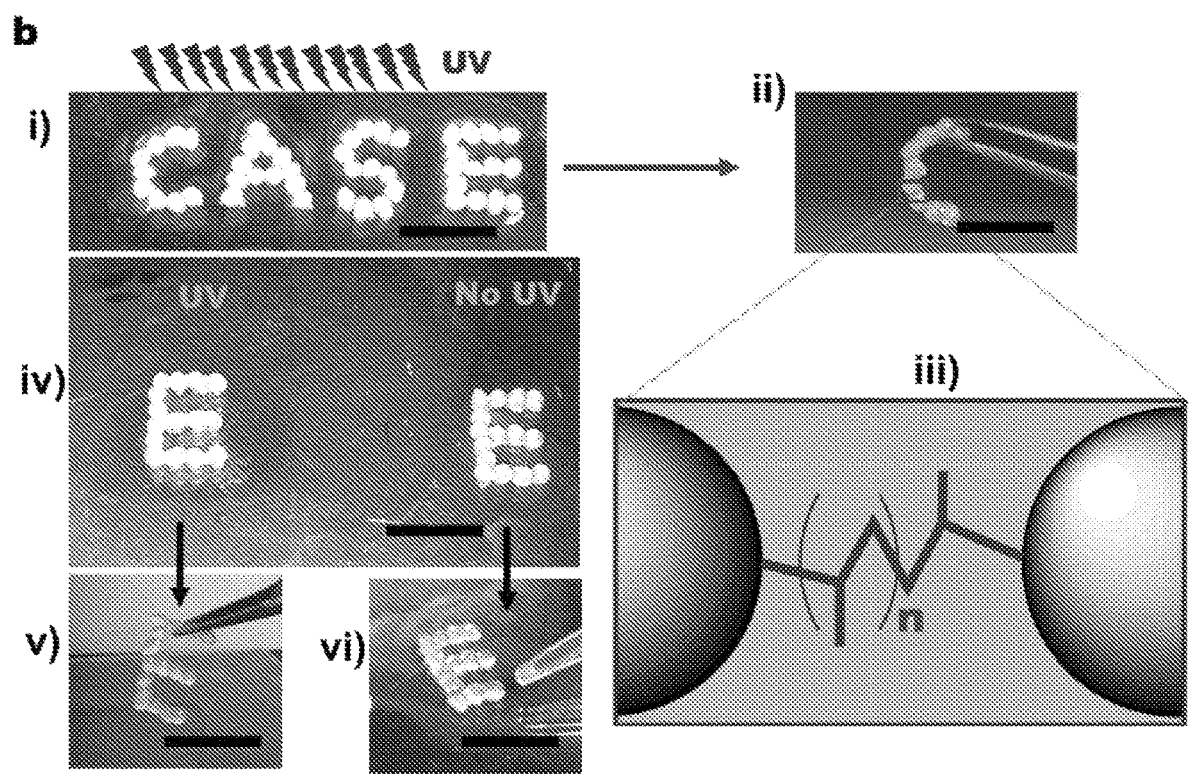

OMA (2.5 w/v %) was dissolved in DMEM (Sigma) with a photoinitiator (2-Hydroxy-4'-(2-hydroxyethoxy)-2-methylpropiophenone, 0.05 w/v %, Sigma) at pH 7.4. OMA solution was loaded into a 5-ml syringe, and then the syringe was installed in a syringe pump (NE-1000X, New Era Pump System Inc.). The OMA solution was pumped at 0.5 ml/sec, and the droplets dripped into a collection bath containing an aqueous solution of CaCl$_2$ (0.2 M) and maintained in the bath for 30 min as shown in FIG. 1A. The resultant OMA beads were collected and washed with DMEM three times. To fabricate magentic microgels, iron (III) oxidze nanoparticles (1 w/v %, size <50 nm, Sigma) were suspended in OMA solution prior to crosslinking. After manually connecting the OMA beads on a glass slide, the resulting OMA bead constructs were exposed to UV light (Omnicure® S1000, EXFO Photonic Solution Inc.) at ~20 mW/cm² for 1 min to stabilize the assembled structures. The magnetic beads were also crosslinked together under UV light at 20 mW/cm² for 1 min after collecting them using an permanet magnet.

hMSC Encapsulated OMA Microgels

Figure 2A:
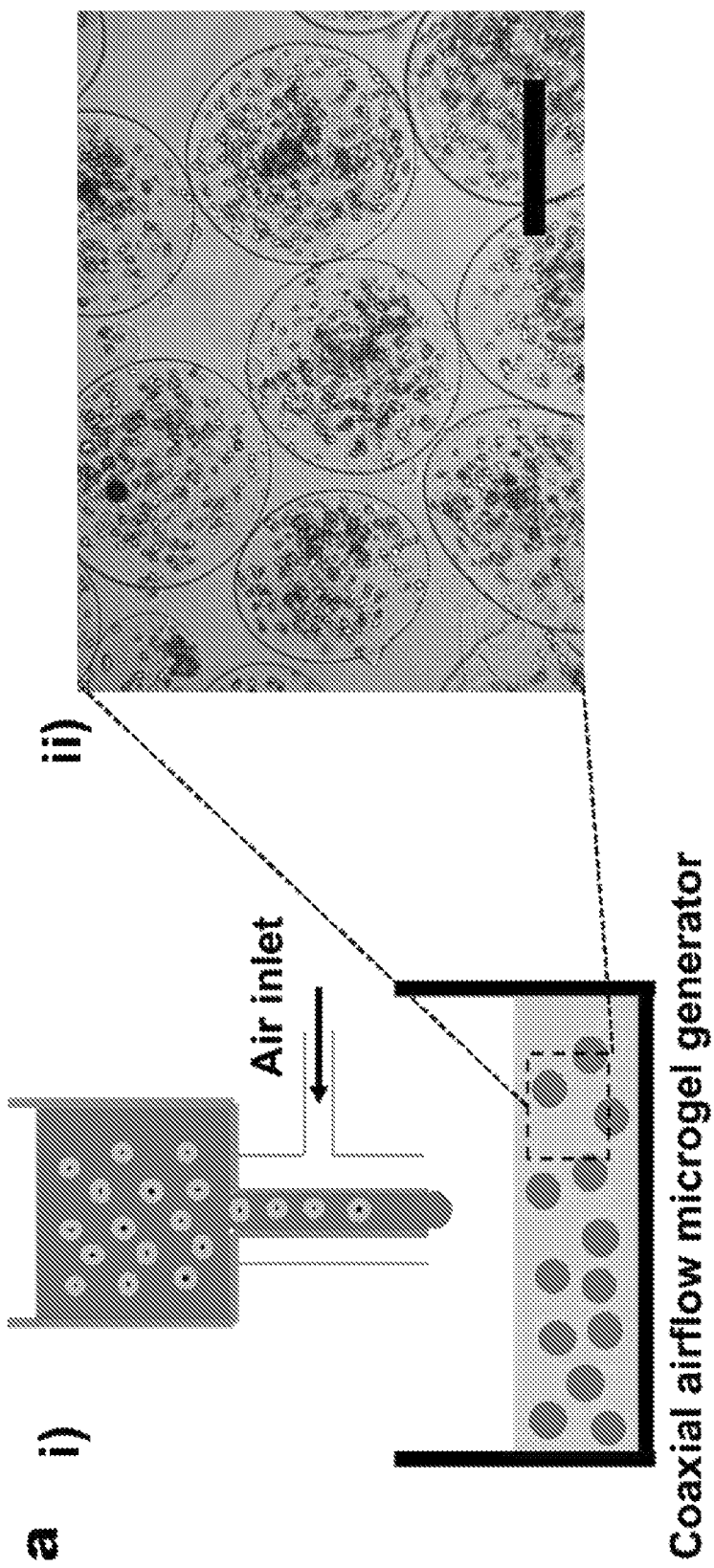
FIGS. 2A-B illustrate the fabrication of hMSC-laden OMA microgels. (A) i) Schematic diagram of coaxial airflow-induced microgel generator and ii) representative photograph of hMSC-laden OMA microgels. (B) Live/Dead staining of encapsulated hMSCs in OMA microgels at day 0. Green color indicates vital cells and red color indicates dead cells. (C) Live/Dead images of hMSC-laden microgels after 4 weeks culture before (i) and after (ii) assembly under UV light. The scale bars indicate 200 μm.
Figure 2B:
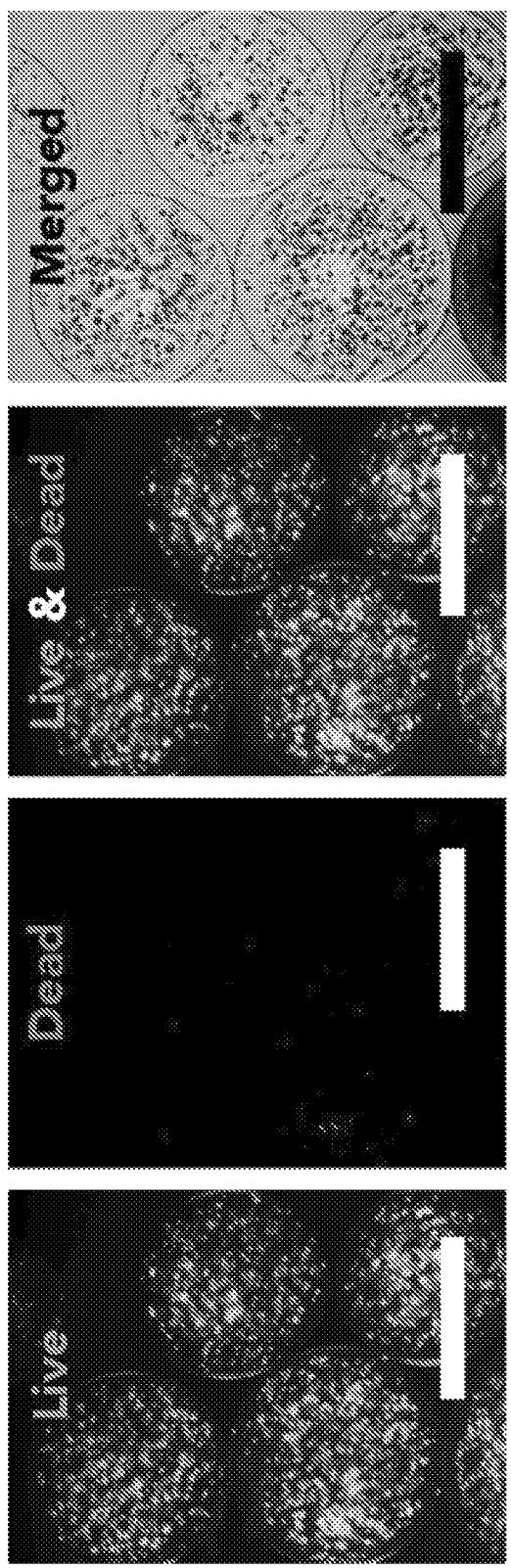
Figure 2C:
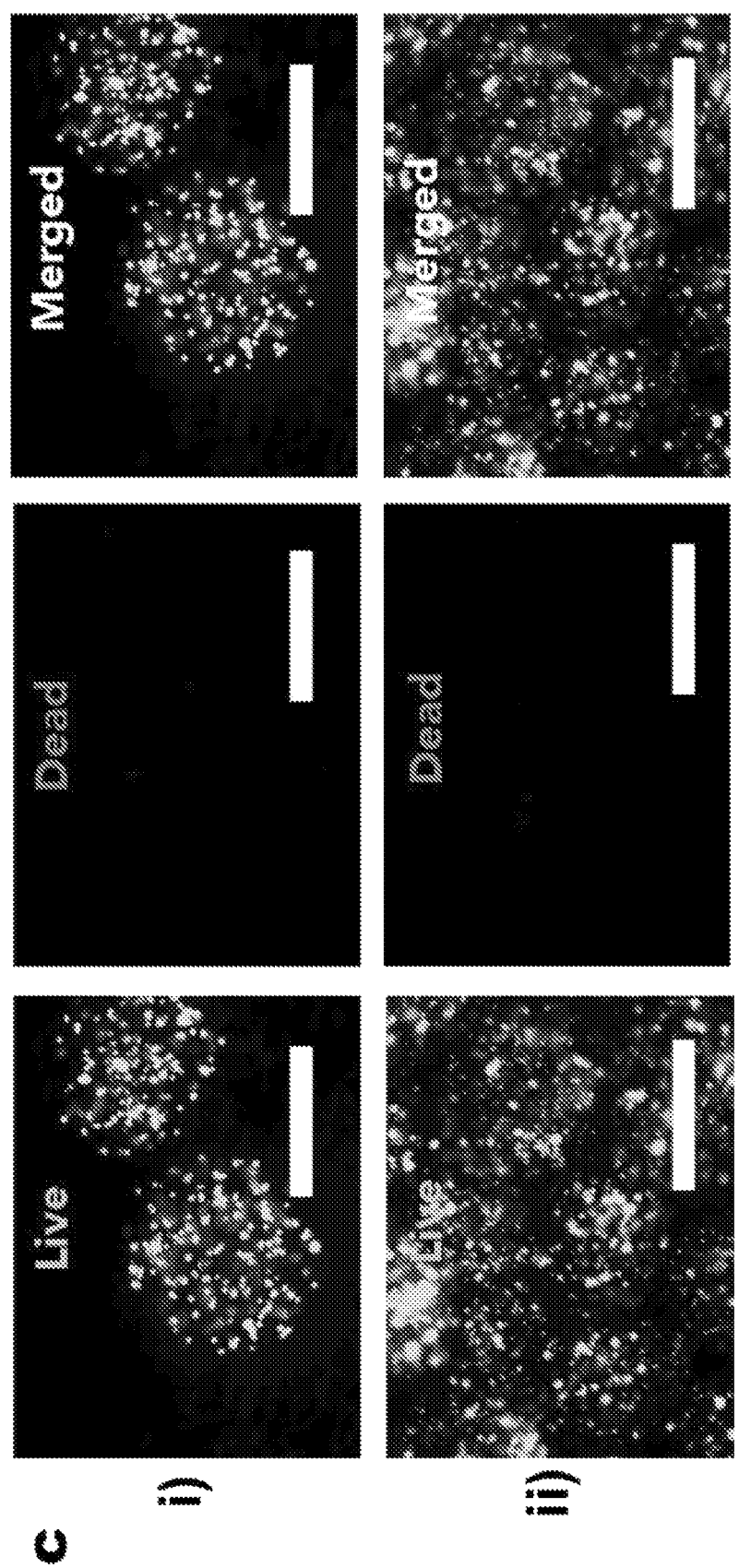
Figure 8:
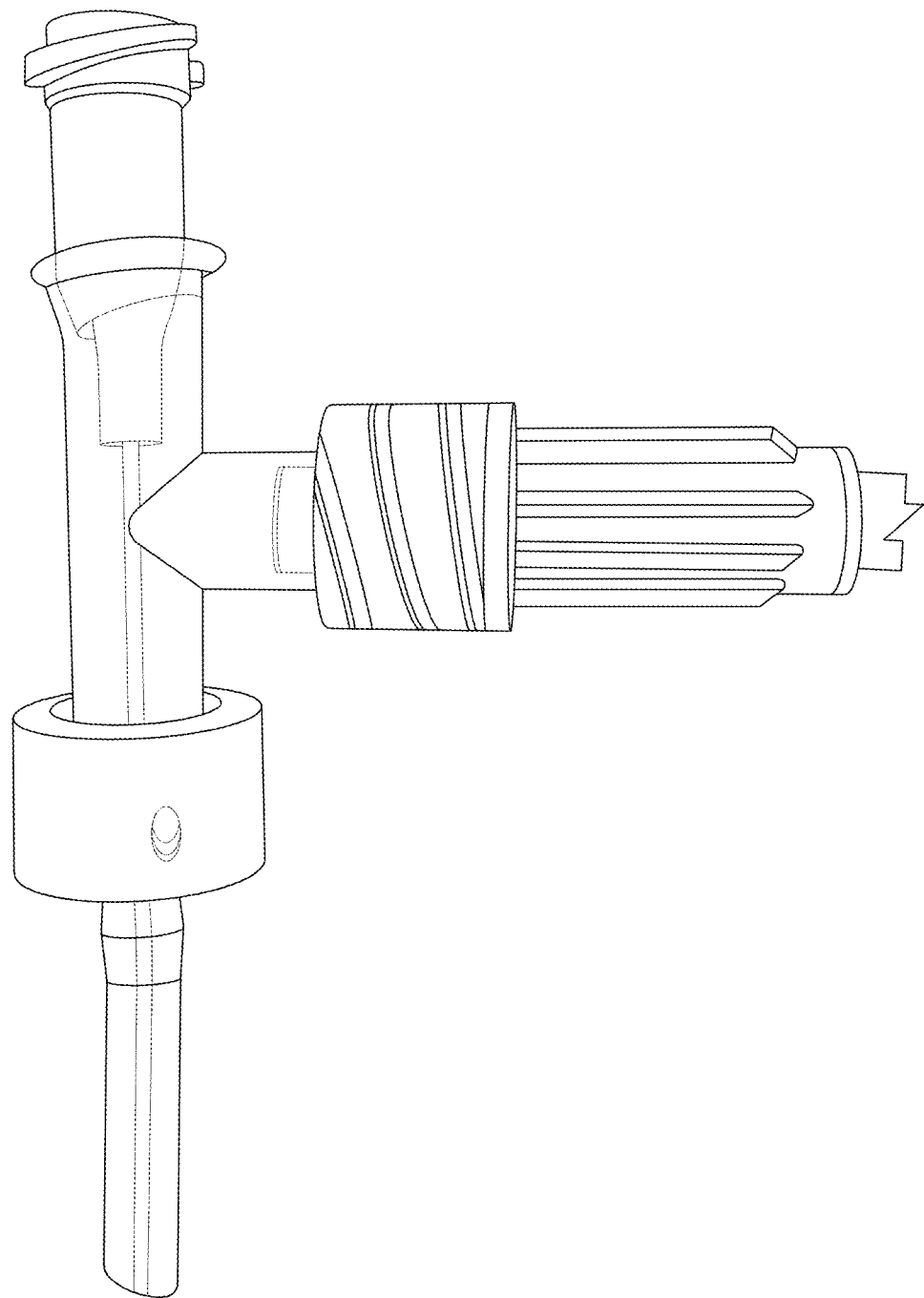
FIG. 8 illustrates a photograph of the custom coaxial airflow-induced microgel generator.

To isolate hMSCs, bone marrow aspirates were obtained from the posterior iliac crest of a healthy twenty three-year old male donor under a protocol approved by the University Hospitals of Cleveland Institutional Review Board. The aspirates were washed with growth medium comprised of low-glucose Dulbecco's Modified Eagle's Medium (DMEM-LG, Sigma) with 10% prescreened fetal bovine serum (FBS, Gibco). Mononuclear cells were isolated by centrifugation in a Percoll (Sigma) density gradient and the isolated cells were plated at $1.8 \times 10^5$ cells/cm² in DMEM-LG containing 10% FBS and 1% penicillin/streptomycin (P/S, Thermo Fisher Scientific) in an incubator at 37° C. and 5% $CO_2$. After 4 days of incubation, non-adherent cells were removed and adherent cell were maintained in DMEM-LG containing 10% FBS and 1 % P/S with media changes every 3 days. After 14 days of culture, the cells were passaged at a density of $5 \times 10^3$ cells/cm². To fabricate hMSC-laden OMA microgels, hMSCs were expanded in growth media consisting of DMEM-LG with 10% FBS (Sigma), 1% P/S and 10 ng/ml FGF-2 (R&D) and suspended in OMA solution (passage 3, $2 \times 10^6$ cells/ml). hMSC-suspended OMA solutions were loaded into an 3-ml syringe, and then the syringe was connected to a coaxial microdroplet generator, designed in our laboratory (FIG. 2A and FIG. 8). The hMSC-suspended OMA solution was pumped at 0.5 ml/sec with an outer air flow rate of 15 L/min, and the droplets dripped into a collection bath containing an aqueous solution of $CaCl_2$ (0.2 M). After fully ionically crosslinking the microgels in the bath for 30 min, the resultant hMSC-laden OMA microgels were collected and washed with DMEM three times. The viability of hMSCs immediately after encapsulation in the OMA microgels was investigated using a Live/Dead assay comprised of fluorescein diacetate [FDA, 1.5 mg/ml in dimethyl sulfoxide (Research Organic Inc.), Sigma] and ethidium bromide (EB, 1 mg/ml in PBS, Thermo Fisher Scientific). The staining solution was freshly prepared by mixing 1 ml FDA solution and 0.5 ml EB solution with 0.3 ml PBS (pH 8). 20 µl of staining solution was added into each 1 ml of microgels suspended in DMEM and incubated for 3-5 min at room temperature, and then stained hydrogel-cell constructs were imaged using a fluorescence microscope (ECLIPSE TE 300) equipped with a digital camera (Retiga-SRV). Unstained hMSC-laden OMA microgels were transferred to 100 ml spinner flasks (Bellco Glass Inc., Vineland, N.J.) containing 80 ml of growth media. The spinner flasks were placed in a humidified incubator at 37° C. with 5% $CO_2$ and stirred at 40 rpm. After 4-week culture, the viability of encapsulated hMSCs in the OMA microgels was again evaluated using the Live/Dead assay before and after assembly of the OMA microgels as described above.

Cryopreservation of hMSC-laden OMA Microgels hMSC-laden OMA microgels that underwent cryopreservation were frozen for one month before being cultured for osteogenic and chondrogenic differentiation. The cryopreservation process was based on the following protocol: hMSC-laden OMA microgels were placed in a polypropylene cryovial (VWR) containing a solution of 10% (v/v) dimethyl sulphoxide (DMSO, Sigma) in growth media at room temperature. The samples were cooled by placing in a conventional freezer (–20° C.) for 1 hr and then moved into a –80° C. freezer. After 12 hours at –80° C., samples were stored inside a liquid nitrogen tank (Statebourne Biosystem) for one month. After 1 month of cryopreservation, the hMSC-laden OMA microgels were thawed rapidly at 37° C., and the viability of encapsulated hMSCs in the OMA microgels was investigated using the Live/Dead assay as described above.

Osteogenic and Chondrogenic Differentiation of the hMSC-laden OMA Microgels

The cryopreserved hMSC-laden OMA microgels were transferred to 100 ml spinner flasks (Bellco Glass Inc., Vineland, N.J.) containing 80 ml growth media. The spinner flasks were placed in a humidified incubator at 37° C. with 5% $CO_2$ and stirred at 40 rpm. After 2 days of culture, the media was replaced with osteogenic differentiation media [10 mM β-glycerophosphate (CalBiochem), 37.5 µg/ml ascorbic acid (Wako USA), 100 nM dexamethasone (MP Biomedicals), and 100 ng/ml BMP-2 in DMEM-high glucose] containing 10% FBS and 1% P/S, or chondrogenic differentiation media [10% ITS+ Premix, 100 nM dexamethasone, 37.5 µg/ml 1-ascorbic acid-2-phosphate, 1 mM sodium pyruvate, 100 µM nonessential amino acids, and 10 ng/ml TGF-$β_1$ in DMEM-high glucose]. The osteogenic and chondrogenic media was changed twice a week. As a comparative group (Fresh group), freshly made hMSC-laden OMA microgels without prior cryopreservation were cultured in spinner flasks containing osteogenic or chondrogenic differentiation media. After 4 weeks of culture, 1 ml of hMSC-laden OMA microgel suspension solution was taken from each spinner flask. After removing media, microgels were homogenized at 35,000 rpm for 30 s using a TH homogenizer (Omni International) in 1 ml ALP lysis buffer (CelLytic™ M, Sigma). The homogenized solutions were centrifuged at 500 g with a Sorvall Legent RT Plus Centrifuge (Thermo Fisher Scientific). For ALP activity measurements, supernatant (100 µl) was treated with p-nitrophenylphosphate ALP substrate (pNPP, 100 µl, Sigma) at 37° C. for 30 min, and then 0.1 N NaOH (50 µl) was added to stop the reaction. The absorbance was measured at 405 nm using a plate reader (VersaMax, Molecular Devices) (N=3). A standard curve was made using the known concentrations of 4-nitrophenol (Sigma). DNA content in supernatant (100 µl) was measured using a Quant-iT Picogreen assay kit (Invitrogen) according to the manufacturer's instructions. Fluorescence intensity of the dye-conjugated DNA solution was measured using a fluorescence plate reader (FMAX, Molecular Devices) set at 485 nm excitation and 538 nm emission (N=3). After an equal volume of 1.2 N HCl was added into each lysate solution, the mixed solutions were centrifuged at 500 g with a Sorvall Legent RT Plus Centrifuge. Calcium content of the encapsulated hMSCs was quantified using a calcium assay kit (Pointe Scientific) according to the manufacturer's instructions. Supernatant (4 µl) was mixed with a color and buffer reagent mixture (250 µl) and the absorbance was read at 570 nm on a microplate reader (VersaMax, N=3). All ALP activity and calcium content measurements were normalized to DNA content. To visualize calcium deposition in the osteogenically differentiated microgels, they were embedded in optimal cutting temperature compound (OCT, Theremofisher), sectioned at a thickness of 20 µm, stained with Alizarin red S, and then imaged using a microscope (Leitz Laborlux S, Leica) equipped with a digital camera (Coolpix 995, Nikon).

After 4 weeks of culture in chondrogenic differentiation media, the viability and morphology of encapsulated hMSCs in the OMA microgels were examined using the Live/Dead assay. Stained microgels were imaged using a fluorescence microscope equipped with a digital camera. For GAG measurement, microgels were homogenized for 60 s in papain buffer (1 mL, pH 6.5)) containing papain (25 μg m/l, Sigma), 1-cysteine ($2\times10^{-3}$M, Sigma), sodium phosphate ($50\times10^{-3}$M) and EDTA ($2\times10^{-3}$M). The homogenate was papain-digested at 65° C. overnight. The following day, GAG was quantified by a dimethylmethylene blue assay and DNA was measured using the PicoGreen assay as described above. To visualize the GAG distribution in the chondrogenically differentiated microgels, microgels were embedded in OCT, sectioned at a thickness of 20 μm, stained with Alcian blue and Toluidine blue O, and then imaged using a microscope equipped with a digital camera. To show the feasibility of heterogeneous assembly of the OMA microgels, osteogenically and chondrogenically differentiated microgels were labeled with red and green fluorescent dyes, respectively. To prepare the green fluorescent dye solution, 1 ml FDA solution was mixed with 0.3 ml PBS (pH 8). Osteogenically differentiated microgels were incubated in the FDA solution for 5 min, and then washed with DMEM containing 0.05 w/v % photoinitiator three times. Chondrogenically differentiated microgels were incubated in 1 ml PBS (pH 7.4) contained rhodamine-phalloidin (1:200 dilution, Thermofisher Scientific) for 60 min, and then washed with DMEM containing 0.05 w/v % photoinitiator three times. Fluorescently labeled microgels were manually heterogeneously assembled and stabilized by photocrosslinking under UV light at 20 mW/cm$^2$ for 1 min.

Rheological Properties of OMA Microgels

Dynamic rheological examination of hMSC-laden OMA microgels was performed to characterize their shear-thinning, self-healing and mechanical properties with a Haake MARS III rotational rheometer (ThermoFisher Scientific). Microgel bioink was prepared by mixing hMSC-laden microgels (10 ml) and OMA solution (3 ml, 4 w/v % OMA, which has 9% actual oxidation and 14% actual methacrylation degree, in DMEM containing 0.05 w/v % photoinitiator), and then excess OMA solution was removed after centrifugation at 500 g with a Sorvall Legent RT Plus Centrifuge. In oscillatory mode, a parallel plate (80 mm diameter) geometry measuring system was employed, and the gap was set to 1 mm After the sample was placed between the plates, all the tests were started at 37±0.1° C., and the plate temperature was maintained at 37° C. An oscillatory frequency sweep (0.01-1.3 Hz; 1% strain) test was performed to measure the storage modulus (G'), the loss modulus (G") and viscosity. An oscillatory strain sweep (0.1-100% strain; 1 Hz) test was performed to show the shear-thinning characteristics of the hMSC-laden OMA microgels and to determine the shear-yielding point at which the hMSC-laden OMA microgels behave fluid-like. To demonstrate the self-healing properties of hMSC-laden OMA microgels, a cyclic deformation test was performed at 100% strain with recovery at 1% strain, each for 1 min at 1 Hz.

Modification of 3D Printer

All 3D printing was performed using a 3D printer modified with a syringe-based extruder. The stock thermoplastic extruder assembly was replaced with a custom-built syringe pump extruder (FIG. 4A). The syringe pump extruder was designed to use the NEMA-17 stepper motor from the original Printerbot thermoplastic extruder and mount directly in place of the extruder on the x-axis carriage. The syringe pump extruder was printed with polylactic acid using the thermoplastic extruder on the printer before its removal. By using the same stepper motor, the syringe pump extruder was natively supported by the software that came with the printer. The design for the syringe pump extruder and the image files of the human femur and skull were downloaded as STL files from the NIH 3D Print Exchange. Digital image files of letters for 3D printing were generated from www.tinkercad.com.

3D Printing of Microgels

For the 3D printing of microgels, the hMSC-suspended OMA solution was pumped at 0.5 ml/sec with an outer air flow rate of 15 L/min, and the droplets dripped into a collection bath containing an aqueous solution of CaCl$_2$ (0.2 M). After crosslinking in the bath for 30 min, the resultant hMSC-laden OMA microgels were collected and washed with DMEM three times. The viability of encapsulated hMSCs in the OMA microgels was investigated as described above. To visualize some of the microgels during printing, microgels were stained with Alizarin red S (2 w/v %) for 30 min, and washed with DMEM three times. For 3D printing of microgels, microgel bioink was prepared as described earlier. The gelatin slurry for supporting bath was prepared as described previously. hMSC-laden microgel bioink was loaded into a 2.5-ml syringe (Gastight Syringe, Hamilton Company) with 0.5-inch 20G stainless steel needle (Mc-Master-Carr). The syringe was then mounted into the syringe pump extruder on the 3D printer. A petri dish filled with gelatin slurry at room temperature as a supporting bath was placed on the building platform. The tip of the needle was positioned at the center and near the bottom of the dish. After 3D printing, printed constructs were stabilized by photocrosslinking under UV at 20 mW/cm$^2$ for 1 min After photocrosslinking, constructs in the gelatin slurry were transfer into preheated DMEM (38° C.). Once the gelatin slurry was melted, printed constructs were rinsed with preheated DMEM three times and placed in a humidified incubator at 37° C. with 5% CO$_2$. The viability of hMSCs in the 3D printed constructs was investigated as described above.

The hMSC-laden OMA microgels were osteogenically or chondrogenically differentiated in spinner flasks for 4 weeks, and stained with Alizarin red S (2 w/v % for 5 min) and Toluidine blue O (0.5 w/v % for 30 min), respectively, washed with diH2O three times, and then used as bioinks. The microgel bioink was prepared and printed into the gelatin slurry as described above. After photocrosslinking under UV light at 20 mW/cm$^2$ for 1 min, constructs in gelatin slurry were transfer into preheated DMEM (38° C.). Once the gelatin slurry was melted, printed constructs were rinsed with preheated DMEM three times and imaged with a digital camera (iPhone 6s).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having decribed the invention, the following is claimed:

1. A method of forming a construct, the method comprising
    providing a composition that includes a plurality of biodegradable dual crosslinkable natural polymer macromers comprising oxidized, acrylated and/or methacrylated alginates and, optionally, a plurality of cells dispersed in the macromers, crosslinking the natural polymer macromers with a first crosslinking agent that crosslinks the oxidized, acrylated and/or methacrylated alginates to form a crosslinked hydrogel comprising a plurality of microgels, wherein the first crosslinking agent is selected from the group consisting of divalent cations, printing the crosslinked hydrogel comprising a plurality of microgels into a defined shape, and optionally crosslinking the singly crosslinked hydrogel with a second crosslinking agent after printing to further stabilize the hydrogel and form the construct.

2. The method of claim 1, the composition further comprising a cryopreservation agent, the composition being cryopreserved and the cells having a substantially equivalent viability and functionality upon thawing compared to similar cells not cryopreserved.

3. The method of clam 1, the hydrogel crosslinked with the second crosslinking agent forming a solid or non-flowing structure with a defined shape.

4. The method of claim 1, wherein the crosslinked hydrogel is printed into a stabilizing bath/gel that is effective to maintain the shape of the printed natural polymer macromers or hydrogel.

5. The method claim 4, wherein the stabilizing bath/gel is removed after crosslinking the hydrogel with the second crosslinking agent.

6. The method of claim 1, wherein the natural polymer macromers are photocrosslinkable with the second crosslinking agent.

7. The method of claim 1, wherein the natural polymer macromers are chemically crosslinked with the second crosslinking agent.

8. The method of claim 1, wherein the hydrogel is cytocompatible and, upon degradation, produces substantially non-toxic products.

9. The method of claim 1, wherein the cells comprise progenitor cells, undifferentiated cells and/or differentiated cells.

10. The method of claim 1, wherein the cells include mesenchymal stem cells.

11. The method of claim 1, further comprising at least one bioactive agent.

12. The method of claim 11, wherein the bioactive agent comprises at least one of BMP-2 or TGF-$\beta$.

13. A method of forming a construct, the method comprising;

providing a composition that includes a plurality of biodegradable dual crosslinkable natural polymer macromers comprising oxidized, acrylated and/or methacrylated alginates and, optionally, a plurality of cells dispersed in the macromers, crosslinking the natural polymer macromers with a first crosslinking agent that crosslinks the oxidized, acrylated and/or methacrylated alginates to form a crosslinked hydrogel comprising a plurality of microgels, wherein the first crosslinking agent is selected from the group consisting of divalent cations, printing the crosslinked hydrogel comprising a plurality of microgels into a defined shape, wherein the crosslinked hydrogel is printed into a stabilizing bath/gel that is effective to maintain the shape of the printed crosslinked hydrogel, and optionally crosslinking the singly crosslinked hydrogel with a second crosslinking agent after printing to further stabilize the hydrogel and form the construct.

14. The method of claim 13, wherein the crosslinked hydrogel is printed into a stabilizing bath/gel comprising gelatin.

* * * * *